United States Patent [19]

Kenyon et al.

[11] Patent Number: 4,933,638
[45] Date of Patent: Jun. 12, 1990

[54] BOREHOLE MEASUREMENT OF NMR CHARACTERISTICS OF EARTH FORMATIONS, AND INTERPRETATIONS THEREOF

[75] Inventors: William E. Kenyon, Ridgefield, Conn.; Peter I. Day, Ridgefield, Conn.; Max Lipsicas, Redding, Conn.

[73] Assignee: Schlumber Technology Corp., New York, N.Y.

[21] Appl. No.: 368,916

[22] Filed: Jun. 19, 1989

Related U.S. Application Data

[63] Continuation of Ser. No. 901,084, Aug. 27, 1986, abandoned.

[51] Int. Cl.$^5$ .................................... G01R 33/20
[52] U.S. Cl. ................................................ 324/303
[58] Field of Search ............... 324/300, 307, 303, 318, 324/322, 346

[56] References Cited

U.S. PATENT DOCUMENTS

| | | | |
|---|---|---|---|
| 3,042,855 | 7/1962 | Brown | 324/303 |
| 3,083,335 | 3/1963 | Schuster | 324/303 |
| 3,289,072 | 11/1966 | Schuster | 324/303 |
| 3,439,260 | 4/1969 | Bene | 324/303 |
| 3,483,465 | 12/1969 | Baker | 324/303 |
| 3,508,438 | 4/1970 | Alger | 324/303 |
| 3,528,000 | 9/1970 | Schwede | 324/303 |

(List continued on next page.)

FOREIGN PATENT DOCUMENTS

2141236-A 12/1984 United Kingdom .

OTHER PUBLICATIONS

Herrick, Couturie & Best, "An Improved Nuclear Magnetism Logging system and its Application to Formation Evaluation", *54th Annual Fall Technical Conference and Exhibition of the Soc. of Petroleum Engineers*

(List continued on next page.)

*Primary Examiner*—Michael J. Tokar
*Attorney, Agent, or Firm*—Peter Y. Lee; Martin M. Novack

[57] ABSTRACT

Borehole NMR logging apparatus and methods, and methods for the interpretation thereof. A logging tool is provided which produces a strong, static and homogeneous magnetic field $B_0$ in a Volume of an adjacent formation on one side of the tool to measure nuclear magnetic resonance characteristics thereof. In the preferred embodiment, the tool has an RF antenna mounted on the outside of the metal body of the tool, directing focussed oscillating magnetic fields $B_1$ at said Volume to polarize or tip the magnetic moments of hydrogen nuclei of fluids within rock pores. The same antenna can be used to receive signals of proton precession in the Volume of interest immediately after transmission of the RF polarizing field $B_1$. Extremely rapid damping of the antenna between the transmitting and receiving modes of operation is accomplished by a Q-switch disclosed herein. The invention provides for the direct measurement of NMR decay having transverse relaxation time $T_2$ behavior, and further provides for the fast repetition of pulsed measurements from within a borehole. An additional magnet array may be mounted offset from the first magnet configuration to prepolarize a formation before it is measured in order to pre-align a larger number of protons than the single magnet configuration could do by itself. Additional features of the invention are disclosed which increase the Signal/Noise ratio of the measured data, and improve the quality and quantity of borehole NMR measurements, per unit of time spent. Disclosed interpretation methods determine fluid flow permeability and longitudinal relaxation time $T_1$-type parameters by directly comparing the measured decay signals (such as $T_2$ and $T_2^*$ type decay) to a representation which responds to both the decay time $t_{dec}$ and the imposed polarization period prior to such decay, $t_{pol}$. The parameters of amplitude and $T_1$ are determined and combined with certain preferred methods to generate robust values of formation characteristics such as fluid flow permeability. Other related methods are disclosed.

16 Claims, 20 Drawing Sheets

U.S. PATENT DOCUMENTS

| | | | |
|---|---|---|---|
| 3,538,429 | 11/1970 | Baker | 324/303 |
| 3,597,681 | 8/1971 | Huckabay | 324/303 |
| 3,667,035 | 5/1972 | Slichter | 324/303 |
| 4,350,955 | 9/1982 | Jackson | 324/303 |
| 4,528,508 | 7/1985 | Vail, III | 324/303 |
| 4,629,986 | 12/1986 | Clow et al. | 324/303 |
| 4,714,881 | 12/1987 | Givens | 324/303 |

OTHER PUBLICATIONS (A.I.M.E., Dallas, Tex., Las Vegas, Nev., Sep. 23–26, 1979).

Farrar & Becker, "Pulse and Fourier Transform Nuclear magnetic resonance", *Academic Press, N.W.*, Chapter 2, pp. 18–33.

Neuman & Brown, "Applications of Nuclear Magnetism Logging to Formation Evaluation", *Journal of Petroleum Technology*, (Dec. 1982), pp. 2853–2860.

Timur, "Pulsed Nuclear Magnetic Resonance Studies of Porosity, Movable Fluid and Permeability of Sand Stones", *Journal of Petroleum Technology*, (Jun. 1969), pp. 775–786.

McDonald & Leigh, "A New Method for Measuring Longitudinal Relaxation", *Journal of Magnetic Resonance*, vol. 9, pp. 358–362 (1973).

Kenyon, Day, Straley & Willemsen, "Compact and Consistent Representation of Rock NMR Data for Permeability Estimation", *61st Annual Technical Conference and Exhibition of the Society of Petroleum Engineers*, Oct. 5–8, 1986, New Orleans.

Seevers, "A Nuclear Magnetic Method for Determining the Permeability of Sandstones", *Society of Professional Well Log Analysts Trans.* (1966), Paper L.

Jackson, "Nuclear Magnetic Resonance Well Logging", *Log Analyst*, Sep.–Oct. 1984, pp. 16–30.

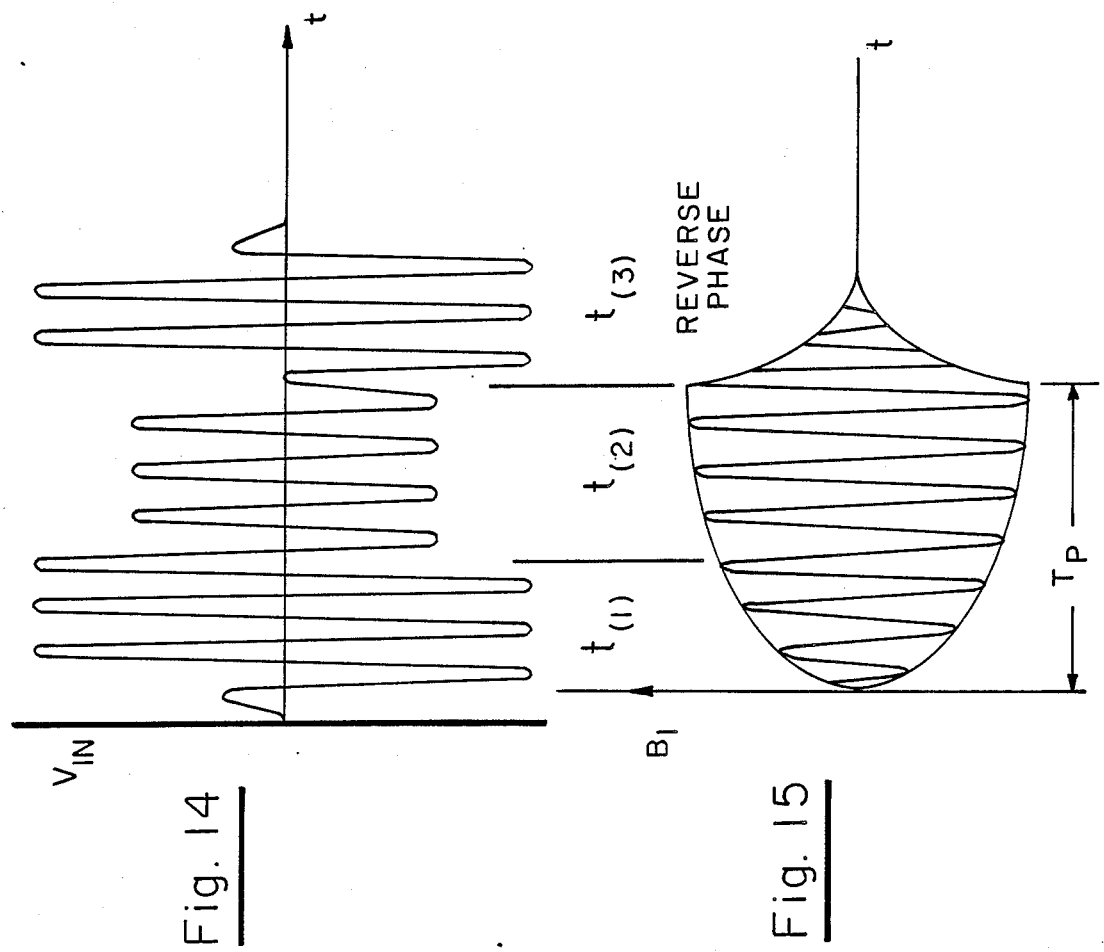
Fig. 14
Fig. 15
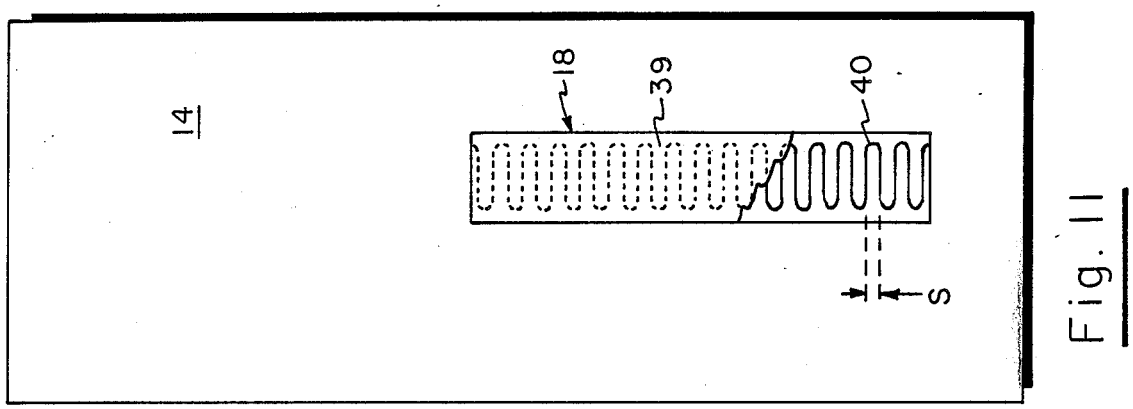
Fig. 11

BOREHOLE MEASUREMENT OF NMR CHARACTERISTICS OF EARTH FORMATIONS, AND INTERPRETATIONS THEREOF

This is a continuation of U.S. application Ser. No. 901,084 filed August 27, 1986, and now abandoned

FIELD OF THE INVENTION

This invention relates to apparatus and techniques for making nuclear magnetic resonance (NMR) measurements in boreholes, and to methods for determining magnetic characteristics of formations traversed by a borehole.

BACKGROUND OF THE INVENTION

Repeated attempts have been made to use the principles of nuclear magnetic resonance to log wells in oil exploration over the past several decades, with limited success. It was recognized that any particles of a formation having magnetic spin, for example atomic nuclei, protons, or electrons, have tendencies to align with a magnetic field which is imposed on the formation. Such a magnetic field may be naturally generated, as is the case with the earth's magnetic field $B_E$ which has an intensity of approximately 0.5 gauss in areas of the globe where boreholes are typically drilled. Any given particle in a formation is additionally influenced by localized magnetic fields associated with nearby magnetic particles, other paramagnetic materials, and the layer of ions which typically line pore walls of certain types of formations such as shales. These localized fields tend to be inhomogeneous, while the earth's magnetic field is relatively homogeneous.

The hydrogen nuclei (protons) of water and hydrocarbons occurring in rock pores produce NMR signals distinct from any signals induced in other rock constituents. A population of such nuclei, having a net magnetization, tends to align with any imposed field such as $B_E$.

When a second magnetic field $B_1$ transverse to $B_E$ is imposed on the protons by a logging tool electromagnet, the protons will align with the vector sum of $B_E$ and $B_1$ after a sufficient polarization time $t_{pol}$ has passed. If the polarizing field $B_1$ is then switched off, the protons will tend to precess about the $B_E$ vector with a characteristic Larmor frequency $\omega_L$ which depends on the strength of the earth's field $B_E$ and the gyromagnetic constant of the particle. Hydrogen nuclei precessing about a magnetic field $B_E$ of 0.5 gauss have a characteristic frequency of approximately 2 kHz. If a population of hydrogen nuclei were made to precess in phase, the combined magnetic fields of all the protons can generate a detectable oscillating voltage in a receiver coil. Since the magnetic moment of each proton produces field inhomogeneities, the precessing protons tend to lose their phase coherence over time, with a characteristic time constant called the transverse or spin-spin relaxation time $T_2$. Furthermore, field inhomogeneities are also produced by other physical phenomena as mentioned above, so that the observed dephasing relaxation time $T_2^*$ is usually shorter than $T_2$. Borehole magnetic resonance measurements of the above type are commercially available as a part of the NML+ service Schlumberger Technology Corporation, Houston, Texas (+Mark of Schlumberger). This tool is capable of measuring the Free Induction Decay of hydrogen nuclei in formation fluids, and to obtain the parameters $T_1$ and $T_2^*$. It does not measure the transverse relaxation time $T_2$. A description of the basic components, operation and interpretation of the commercial logging tool used in the NML service is contained in a paper entitled, "An Improved Nuclear Magnetism Logging System and its Application to Formation Evaluation", by R. C. Herrick, S. H. Couturie and D. L. Best, presented at the 54th *Annual Fall Technical Conference and Exhibition of the Society of Petroleum Engineers* (A.I.M.E., Dallas, Texas) in Las Vegas, Nevada, September 23-26, 1979; this paper, appended hereto, is incorporated herein by reference.

Other sequences of magnetic fields can be imposed on a population of protons in a formation, to measure other characteristics thereof. For example, if a pulse of alternating current having a frequency f is passed through a transmitter coil, producing an oscillating polarizing field $B_1$ perpendicular to a static field $B_o$, a population of protons precessing at a Larmor frequency equal to f would tend to align at an angle to $B_1$. At the end of the pulse, when $B_1$ is removed, the aligned protons experience a perpendicular torque, and precess about the $B_o$ vector. After a characteristic time called the longitudinal or spin-lattice relaxation time $T_1$, the protons have relaxed to thermal equilibrium, wherein a weighted percentage of protons are aligned in the direction of $B_o$. Various other sequences of imposed magnetic fields can be used, as is discussed in T. C. Farrar and E. D. Becker, "Pulse and Fourier Transform Nuclear Magnetic Resonance", Academic Press, N.Y. (1971), Chapter 2, pp. 18-33, which is incorporated herein by reference.

Although measurements of NMR characteristics of rock samples can be accurately made in a laboratory, making comparable measurements in a borehole is greatly exacerbated by the hostile environment where temperatures may reach several hundred degrees Fahrenheit, pressures reach thousands of p.s.i. and all of the equipment must be packed within a cylindrical volume of only several inches diameter.

One of the earliest NMR logging tools is shown in U.S. Pat. No. 3,289,072 granted November 29, 1966 to N. A. Schuster. A strong electromagnet is used to subject a sample of water or oil to a predetermined magnetic field. A RF coil produces an oscillating second magnetic field which causes nuclear magnetic resonance of protons in the sample and resonance of similar protons in the adjacent formation. Schuster proposed the use of a multipole electromagnet mounted in a wall engaging pad, or alternatively a larger electromagnet mounted within the logging sonde, to produce a static magnetic field $B_0$. Schuster has also proposed other configurations of electromagnets and detection RF coils, for example in U.S. Pat. No. 3,083,335 granted on March 26, 1963, wherein the coil is positioned within a gap between two opposite poles of two bar magnets. Here, the magnetic field lines of the coil intersect field lines of the bar magnets perpendicularly, which is the optimum angle for inducing nuclear magnetic precession.

A more recent U.S. Pat. No. 3,667,035 granted May 30, 1972 to C. P. Slichter, shows a similar configuration of two coaxially aligned bar magnets and a RF coil positioned within the gap between opposite poles of the magnets. The term "bar magnet" is used herein to mean any magnet having only one north pole and one south pole, facing opposite directions, and may be either a permanent magnet or an electromagnet. Both the Slichter design and the Schuster design use electromagnets which require inconveniently large D.C. currents to be transmitted to a logging sonde through many thousands of feet of electrical cable.

U.S. Pat. No. 3,528,000 granted September 8, 1970 to H. F. Schwede shows one type of NMR logging tool in FIGS. 8 and 9, wherein a permanent magnet produces a first magnetic field which is fixed in its intensity, and an inductive coil produces an oscillating magnetic field whose frequency is varied over a selected range. Since the first magnetic field is produced by two opposite magnetic poles (one N and one S) placed side by side, the field is not homogeneous and the spatial gradient of the field is evidently non-zero at all points in the formation. In addition, since the first and second fields intersect not only in the formation, but also within the borehole, it is evident that protons constituting water or hydrocarbons within the borehole fluid contributes to signals detected by the RF coil, and must be removed either electronically or by chemically treating the borehole fluid, if a true formation measurement is desired.

Other NMR logging tools have been proposed which use permanent bar magnets, aligned coaxially in a logging sonde with a detection coil positioned in the gap between the magnets, for example as shown in U.S. Pat. No. 3,597,681 granted August 3, 1971 to W. B. Huckabay.

Another permanent magnet configuration has been proposed in U.S. Pat. No. 4,350,955 granted September 21, 1982 to J. A. Jackson, wherein two permanent bar magnets are coaxially aligned such that the RF detection coil is positioned in the gap between two similar poles of the two magnets. Similarly, United Kingdom Patent Application No. 2,141,236-A, published December 12, 1984, shows a similar configuration of coaxially aligned bar magnets with a detection coil positioned in a gap between the magnets. This type of configuration produces a toroidal region of homogeneous magnetic field wherein nuclear resonance may be measured. However, these tools may be adversely affected by signals from the borehole fluid in a large or deviated borehole where the tool would tend to lean against one side wall of the borehole. If the tool is designed to produce the toroidal region far away from the tool body, the produced magnetic field becomes much weaker, resulting in a significantly weaker signal. This configuration further requires that the detection coil or antenna be enclosed by a structure which would not block the oscillating electromagnetic waves of the measured signal. For example, fiberglass or some other non-metallic material is typically used; unfortunately, this structurally weakened link decreases the structural integrity of the tool and renders it considerably less useful in rough borehole conditions.

NMR measurement of particles other than hydrogen nuclei having magnetic spin have also been proposed. U.S. Pat. No. 3,439,260, granted April 15, 1968 to G. J. Benn et al, for example, discloses techniques of measuring magnetic resonance of carbon-13 nuclei in earth formations.

Other representative U.S. patents which have been granted for NMR logging tools and techniques include the following: 3,042,855 to R. J. S. Brown; 3,508,438 to R. P. Alger et al.; 3,483,465 to J. H. Baker, Jr.; 3,505,438 to R. P. Alger, et al.; 3,538,429 to J. H. Baker, Jr.; 4,035,718 to R. N. Chandler.

Each of the NMR logging tools which have been proposed or constructed has had practical deficiencies. All of them had to deal with the fundamental difficulties of making this kind of delicate measurements under severe conditions of temperature, pressure, and physical trauma typical of logging runs in oil wells. Furthermore, since the concentration of hydrogen nuclei within the borehole is much higher than the concentration in any rock formation, the undesirable NMR signals arising in a borehole are potentially much higher than any signals from surrounding formations. In order to alleviate this troubling phenomenon, it has been known in the art to treat the borehole fluid with a paramagnetic substance such as magnetite, and to circulate the treated fluid throughout the borehole before a logging run is made so that the relaxation time of hydrogen nuclei in the borehole is shortened by so much that its contribution to the NMR measurement is eliminated. Such pretreatment of borehole fluid is expensive and time consuming. Pretreatment may also introduce the same chemical, via the borehole, into adjacent permeable formations, and thus distort measurements.

It has also been recognized that those NMR logging tools which require powerful electromagnets tend to be unreliable because the high power currents flowing through the tool inevitably tend to break down various electronic components such as switches, especially under the high temperature environment in boreholes. The previous tools all required that the sonde or pad body be constructed of a non-metallic material such as fiberglass, synthetic rubber or teflon to enable detection of A.C. signals. These materials are considerably weaker than the alloy metals which are normally used in constructing other types of logging tools. The inability to use a strong metallic superstructure in constructing NMR logging tools has further contributed to their relative unpopularity in the industry.

Previous NMR logging tools typically required approximately 20–30 milliseconds, called "dead time", after a polarizing field pulse is shut and before the transmitting coil is sufficiently damped to permit measurements to be taken. During this dead time, considerable information of magnetic relaxation is irretrievably lost, and the S/N ratio is considerably degraded.

The commercially available NMR logging tool cannot directly measure the spin-spin relaxation time $T_2$. Instead, the existing commercial tool obtains measures of the Free Fluid Index (FFI) and the observable dephasing relaxation time $T_2^*$, also called the free induction decay time constant. Various log interpretation techniques may be used to derive other useful information as discussed in, e.g. "Applications of Nuclear Magnetism Logging to Formation Evaluation" by C. H. Neuman and R. J. S. Brown, *Journal of Petroleum Technology* (Dec. 1982) pp. 2853–2860, and in the Herrick et al. paper cited above.

Interpretations

The basic purpose of making NMR measurements in boreholes is to obtain information of formation constituents surrounding the borehole. Such information typically relate to magnetic relaxation times of the hydrogen nuclei in water and hydrocarbons, but it also can relate to other physical parameters or other particles in the formation.

It is known that, subsequent to the imposition and removal of a magnetic polarizing field, a population of hydrogen nuclei or protons undergoes relaxation in several modes, as discussed in the previously cited references. As explained in Herrick, et al. above, the NML tool imposes a strong DC polarizing field $B_p$ to the formation to align proton spins approximately perpendicular to the earth's field $B_E$. During the "Normal Mode" operation of the tool, the polarizing field is applied for a period roughly five times $T_1$ to polarize formation protons to saturation. A large polarizing current (with a power on the order of 1 KW) is shut off and, after the coil has been fully damped, requiring about 25 milliseconds, measurement circuits are coupled to the coil to detect signals induced therein by the population of protons in the formation which now freely precess about the earth's magnetic field $B_E$. This Free Induction Decay signal, called the "FID" has a frequency equal to the Larmor frequeny $\omega_L$ in the earth's field which is about 2 kHz, as shown in FIG. 20. The basic NMR measurement, then, is an induced voltage in a conductive coil located in the borehole. The amplitude, frequency and phase of this voltage signal must then be correlated with secondary parameters which tell us something about the magnetic characteristics of the measured population of protons, namely $T_1$, $T_2$, $T_2$*. The secondary parameters, to be of use, must then be linked to an interpretations method which obtains desired information such as the fluid porosity, viscosity, permeability, or water cut of the measured formation.

* (Mark of Schlumberger)

Referring to FIG. 20, it has been known in the prior art to measure the decay envelope of the 2 kHz free induction decay signal, and then to extrapolate the envelope to the initial time $t_o$ at which the polarizing pulse $B_p$ was shut off. The voltage amplitude at $t_o$, when multiplied by calibration constants which depend on design parameters of the particular tool, yields the Free Fluid Index (FFI) also called the free fluid porosity ($\Phi_f$). The FID decay curve is known to be associated with the observable dephasing time constant $T_2$*.

The NML tool can also be used in a "$T_1$ Stationary Mode" of operation wherein a plurality of non-saturating polarizing pulses are applied to the formation while the tool remains stationary in the borehole at the measuring depth. Referring to FIG. 21, the free induction decay signal is measured and a decay envelope estimated, as before, to extrapolate the formation magnetization at the time $t_0$ when the polarizing pulse was shut off, and this is successively done for each period of polarization, a, b, c and d. The greater the polarizing period, the more formation protons are aligned with the polarizing field $B_p$ and the higher the resultant net magnetization These polarization pulses should be non-saturating, since the maximum magnetization $M(t_0)$ and the FID curves following saturating pulses would be identical and redundant. The extrapolated values of magnetization at the instant after shut-off of the polarizing field, $M(t_0)$, is then plotted against the period of polarization to obtain a $T_1$ Build-Up curve which has a characteristic time constant equal to the longitudinal relaxation time $T_1$. In prior interpretation methods, $T_1$ typically was estimated by fitting the $T_1$ Build-Up curve to an exponential decay function, using commercially available "least squares fit" computer programs.

Although only four points are shown in FIG. 21, it is known in the art to make up to eight separate sets of FID measurements and obtain corresponding values of maximum magnetization $M(t)$. The motivation for extracting $T_1$ is based on a desire to determine the fluid flow permeability, k, using certain known correlations between k and $T_1$, as is discussed in the literature, e.g., A. Timur, "Pulsed Nuclear Magnetic Resonance Studies of Porosity, Movable Fluid and Permeability of Sand Stones", *Journal of Petroleum Technology* (June 1969), pp. 775-786.

Because the S/N ratio of each measured $T_2$* decay signal is not very high, coupled with the problem that proton precession during the first 20-30 milliseconds after the polarizing pulse shut off cannot be measured, it is seen that significant errors can be introduced in the estimated value of magnetization at $t_0$. The resultant $T_1$ Build-Up curve that is fitted to the data may suffer from large errors, and the extracted parameter $T_1$ tends to be undependable.

For many of the above reasons, the prior logging tools and interpretation methods have not been capable of determining formation characteristics with sufficient accuracy and dependability to become fully accepted by the industry.

Accordingly, it is an object of the present invention to provide improved apparatus and methods for determining magnetic characteristics of earth formations more accurately and more dependably.

It is an additional object of the invention to provide apparatus and methods to determine the nuclear magnetic relaxation time, the free fluid porosity, permeability and related pore fluid characteristics of earth formations traversed by a borehole.

It is also an object of the invention to provide borehole apparatus for measuring magnetic resonance which can be constructed of strong metallic materials, which can operate repeatedly in borehole conditions with high reliability, and which can accurately measure formation characteristics without requiring any pretreatment of the borehole fluid with magnetic substances.

It is a further object of the invention to provide a magnet configuration for NMR measurements which has a simple, sturdy construction, and which is easily and conveniently tested, calibrated and used in logging a borehole.

It is also an object of the invention to provide a magnetic resonance logging tool which directly measures the transverse relaxation time $T_2$ of formations traversed by a borehole.

In another aspect of the invention, it is an object to provide improved methods for determining the permeability and like parameters from measured free induction decay signals of NMR logging tools.

It is also an object of the invention to provide improved methods for determining the magnetic relaxation times of a measured population of particles in earth formations surrounding a borehole.

SUMMARY OF THE INVENTION

In accordance with the present invention, apparatus is provided which produces a static and substantially homogeneous magnetic field focussed into a formation on one side of the logging tool. By directing and configuring the combined magnetic fields of a configuration of magnets, wherein the spacial field gradient substantially vanishes, thereby insuring that the field is highly homogeneous throughout that region. In a preferred form, the magnets are mounted within a skid or logging pad, the static magnetic field is directed through the face of the pad into an adjacent formation, and the region of substantially homogeneous field is situated in a volume of formation behind the mudcake layer which typically lines borehole walls. A homogeneous magnetic field several hundred times stronger than the earth's magnetic field can be thus imposed, or "focused", on a volume of formation in situ.

In one aspect of the present invention, the RF antenna is mounted on the outside of the metallic structure of the tool so that the tool body serves as a natural shield against any signals which may be generated by resonant conditions behind the body, particularly those potentially strong resonance signals from borehole fluid. In the preferred form, the antenna is configured to focus its signals radially outwardly from the pad face, into the volume of formation having the homogeneous field, thereby additionally reducing the distortion of measured signals from borehole effects. As a consequence of this distinctive feature of the invention, the logging apparatus may be constructed of strong metallic alloys, unlike prior art tools, and the present measurement technique actually uses the shielding effect of a metal sonde to good advantage, to enhance the S/N ratio of NMR measurement. Since borehole effects are excluded by the dual focussed design, it is no longer necessary to pretreat the borehole fluid with paramagnetic chemicals.

In accordance with a preferred form of the invention, an elongated trough antenna is provided on a pad face, parallel to the borehole axis and to an elongated volume of substantially homogeneous static magnetic field in the adjacent formation. By superposing the geometric shape of the volume of homogeneous and static field with the pattern of the RF field from the antenna, near optimum resonance conditions can be created. In the preferred embodiment the static field is directed radially into said volume, while the RF field is circumferentially directed and thus perpendicular to the static homogeneous field within the volume of investigation. The length of the trough antenna is preferably about equal to the length of the volume of investigation.

In accordance with the present invention, methods and apparatus are provided for making fast pulsed measurements of magnetic resonance in earth formations surrounding a borehole, particularly the direct measurement of spin-spin relaxation time $T_2$, to determine formation characteristics.

In accordance with a further aspect of the invention, the transmitting antenna is also used for receiving magnetic resonance signals, and special circuitry is used to very rapidly damp the ringing current which occurs in the antenna after a power shut-off. The special circuitry, called a Q-Switch, damps the polarizing antenna current about 1000 times faster than the previous tool, and enables many pulses to be injected successively into a formation in a short period of time.

By vastly increasing the number of measurement cycles per unit time, the present invention enables the logging tool to: (1) increase the S/N of the overall measured data set, thereby permitting either a faster logging rate or continuous logging; and (2) reduce the NMR measurement time during which nuclei may diffuse within rock pores, thereby reducing the undesirable magnetic effects of such diffusion.

In accordance with another aspect of the invention, additional apparatus is provided to prepolarize a formation volume of interest before the main magnetic configuration reaches proximity to the formation. The prepolarization field is preferably much stronger than that of the main magnet configuration, and serves to increase the population of protons that is aligned in the $B_0$ vector direction, and thus further increases the magnetic precession signal level.

In accordance with yet another aspect of the invention, small currents are introduced in the vicinity of a measuring tool to alter the static field during part of the measurement cycle to spoil the signals from these localized regions. In the preferred embodiment, the small currents flow through a wire preferably configured as a loop covering the antenna opening and attached parallel to the wall-engaging face of the tool. This configuration serves to significantly reduce or eliminate any resonance signals produced by borehole mud or mudcake immediately adjacent to the antenna surface, and substantially reduces undesirable signals. The spatial extent and magnetic effects of these field inhomogeneities can be carefully controlled by selecting the spacing of adjacent sectors of the wire, the current, and other relevant dimensions. In a different aspect of the invention, the wire or its equivalent can be used to produce magnetic field gradients extending into the volume of measured resonance, which permits other advantageous magnetic measurements to be made.

In another aspect of the invention, methods are provided for interpreting the measured data, such as free induction decay signals, pulse sequence type magnetization curves, and other magnetic resonance measurements, to determine the values of formation pore fluid characteristics such as permeability.

For other objects and advantages of the invention, and to provide a fuller understanding thereof, reference is made to the following description taken in conjunction with the cited references and the accompanying drawings.

BRIEF DESCRIPTION OF THE DRAWINGS

FIG. 11 is an enlarged front view of the wall engaging face of the logging tool shown in FIG. 1, partially cut away to show the antenna and a meandering wire of the present invention;

FIG. 14 is a diagram showing representative signals input to the amplifier shown in FIG. 9 and FIG. 12;

FIG. 15 is a diagram showing the pulse shape of an exemplary oscillating magnetic field $B_1$ produced by the antenna of FIG. 9;

DESCRIPTION OF PREFERRED EMBODIMENTS

Figure 1:
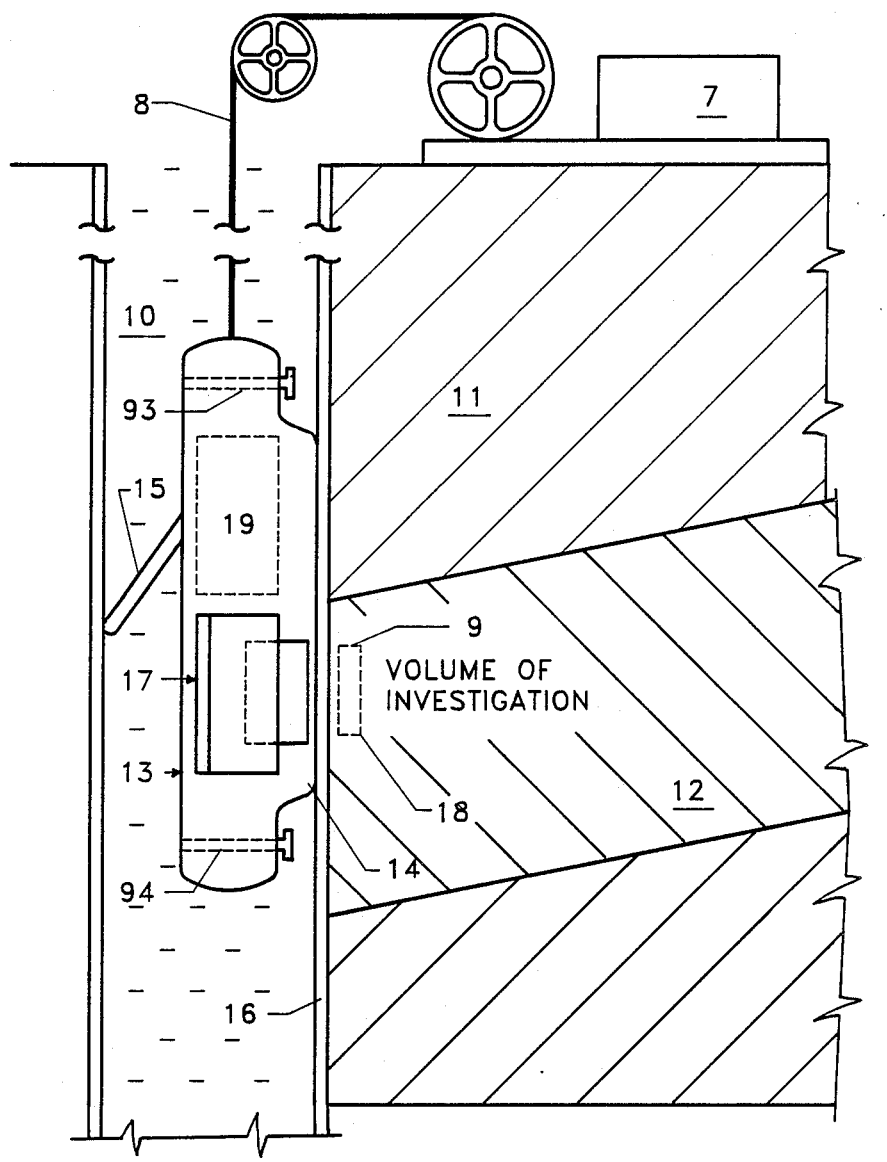
FIG. 1 is a side view of a NMR logging tool positioned in a borehole for making measurements of surrounding formations, in accordance with the present invention.

Referring to the drawings and particularly FIG. 1 thereof, a borehole 10 is shown adjacent to formations 11, 12, the characteristics of which are to be determined. Within borehole 10 there is shown a logging tool 13 connected via a wireline 8 to surface equipment 7. Tool 13 preferably has a face 14 shaped to intimately contact the borehole wall, with minimal gaps or standoff. The tool 13 also has a retractable arm 15 which can be activated to press the body of the tool 13 against the borehole wall during a logging run, with the face 14 pressed against the wall's surface.

Although tool 13 is shown in the preferred embodiment of FIG. 1 as a single body, the tool may obviously comprise separate components such as a cartridge, sonde or skid, and the tool may be combinable with other logging tools as would be obvious to those skilled in the art. Similarly, although wireline 8 is the preferred form of physical support and communicating link for the invention, alternatives are clearly possible, and the invention can be incorporated in a drill stem, for example, using forms of telemetry which may not require a wireline.

The formations 11, 12 have distinct characteristics such as formation type, porosity, permeability and oil content, which can be determined from measurements taken by the tool. Deposited upon the borehole wall of formations 11, 12 is typically a layer of mudcake 16 which is deposited thereon by the natural infiltration of borehole fluid filtrate into the formations.

In the preferred embodiment shown in FIG. 1, tool 13 comprises a magnet array 17 and an antenna 18 positioned between the array 17 and the wall engaging face 14. Magnet array 17 produces a static magnetic field $B_0$ in all regions surrounding the tool 13. The antenna 18 produces, at selected times, an oscillating magnetic field $B_1$ which is focussed into formation 12, and is superposed on the static field $B_0$ within those parts of formation opposite the face 14. The Volume of Investigation of the tool, shown in dotted lines in FIG. 1, is a vertically elongated region directly in front of tool face 14 in which the magnetic field produced by the magnet array 17 is substantially homogeneous and the spatial gradient thereof is approximately zero.

A prepolarizing magnet 19, shown in dotted lines, may be positioned directly above the array 17 in a modified embodiment of the invention which will be separately discussed.

The tool 13 makes a measurement by magnetically tipping the nuclear spins of particles in formation 12 with a pulse of oscillating field $B_1$, and then detecting the precession of the tipped particles in the static, homogeneous field $B_0$ within the Volume of Investigation, over a period of time. As seen in FIG. 1, this Volume of Investigation does not overlap the surface of the wall engaging face 14 as in some previous logging tools, and does not overlap the mudcake 16 on the borehole wall.

In a pulse echo type of measurement, as discussed in detail in the previously cited book of Farrar and Becker, for example, a pulse of RF current is passed through the antenna 18 to generate a pulse of RF field $B_1$ where the RF frequency is selected to resonate only hydrogen nuclei subjected to a static field strength equal to the field $B_0$ within the Volume of Investigation. The signals induced in antenna 18 subsequent to the RF pulse represent a measurement of nuclear magnetic precession and decay within the Volume, automatically excluding any undesirable contributions from the borehole fluid, mudcake, or surrounding formations where the field strength of $B_0$ is different.

In devising the preferred embodiment of the invention, applicants have sought to optimize the signal-to-noise (S/N) ratio of the measurement process. As will be appreciated by those skilled in the art, the following discussion helps to explain the principal parameters to be considered in making the preferred embodiment of the invention.

Figure 2:
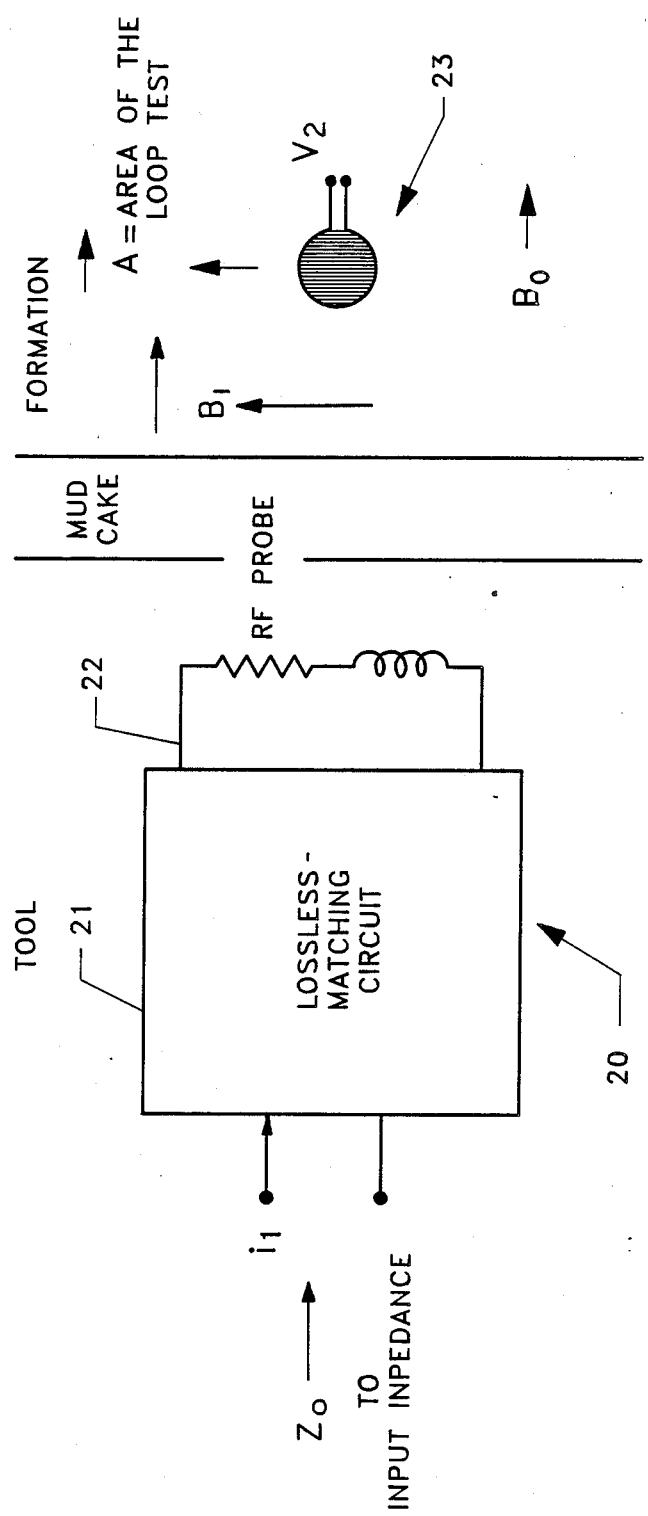
FIG. 2 is a conceptual schematic diagram representing the measurement system of the tool of FIG. 1.
Figure 3:
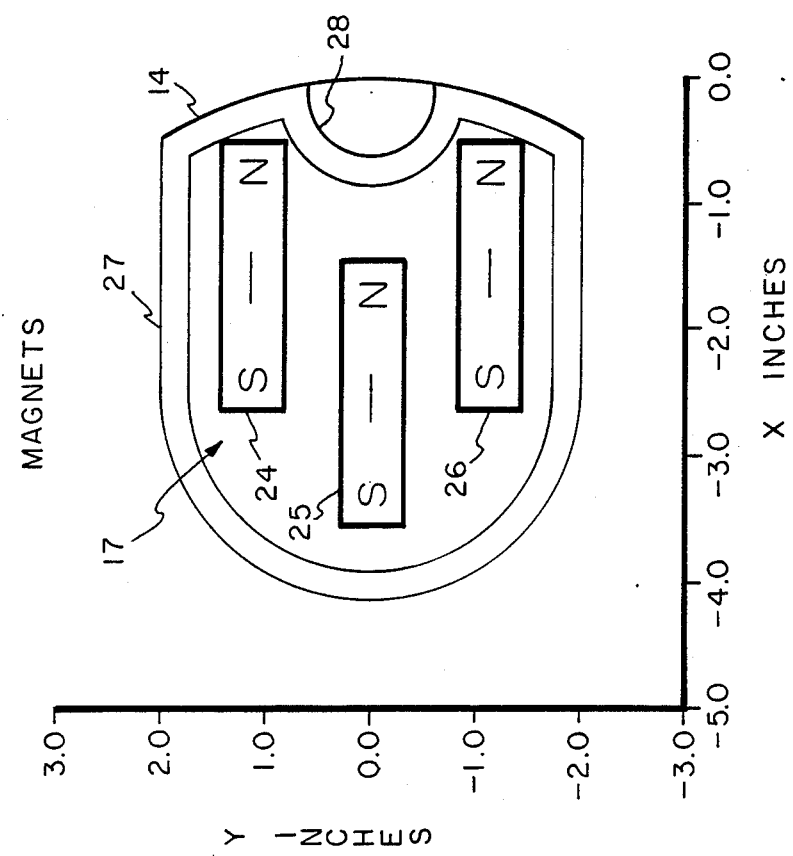
FIG. 3 is an enlarged cross-sectional plan view of a magnet array used in the preferred embodiment of the present invention shown in FIG. 1.

Referring to FIGS. 2 and 3, in considering the signal strength of a nuclear magnetic resonance measurement made by tool 13 in the adjacent formation 12, it is helpful to treat the interaction of antenna 18 with the magnetic moment of the formation as parts of a single four terminal network to which the Reciprocity Theorem can be applied. The network 20, having an input impedance $Z_0$, comprises a lossless matching circuit 21 and an RF probe or antenna 22 which is shown simply as having a resistance and inductance in series. An oscillating current $I_1$ of frequency $\omega$ flows through RF probe 22, producing an oscillating magnetic field $B_1$ in the formation including the Area within a test loop 23. The voltage that is induced in test loop 23 as a result of the current $I_1$ is given by $$V_2 = Z_{21} I_1 = -i\omega A \cdot B_1 \tag{1}$$

where $Z_{21}$ is the cross impedance between the antenna current and the voltage induced in the test loop 23.

Now assume that a current $I_2$ is impressed upon the test loop, and induces a voltage $V_1$ at the terminals of the matching network 20, which is $$V_1 = Z_{12} I_2 \tag{2}$$

Where $Z_{12}$ is the cross impedence between the test loop current and the voltage induced in the antenna 22. Invoking the Reciprocity Theorem, $Z_{12} = Z_{21}$, we obtain.

$$V_1 = -i\omega A \cdot (B_1/I_1) I_2. \tag{3}$$

Since the magnetic moment of the loop 23 is $m = I_2 A$, the magnetization dM of a volume dV is $dM = I_2 A\, dV$. The net signal from the entire formation can be derived form the above and represented as $$V_s = -i \int dV \omega M \cdot (B_1/I_1) \tag{4}$$

where the integral is taken over the volume in which the resonance condition $B_0 = \omega/Y$ is satisfied. In order to optimize the measured signal response of the present NMR tool, we may assume that the volume of NMR investigation has an area $A_R$ and a length $L$, and that the integrand is constant within this volume. In practice, we have found this assumption to be a fairly good approximation. By making the substitutions $\omega = YB_0$ and $M = \chi B_0/\mu_0$ in the above equation, where $Y$ is the gyromagnetic ratio, $\mu_0$ is the magnetic permeability of free space, and $\chi$ is the nuclear magnetic susceptibility of protons in the formation, we derive $$V_S = \frac{\chi Y}{\mu_o} B_0^2 \left( \frac{B_1}{I_1} \right) A_R L \tag{5}$$

Now we want to estimate the size of the area $A_R$ for actual magnetic configurations such as that of the magnet array 17 shown in FIG. 1. As will be further discussed hereinbelow, magnet array 17 produces a static magnetic field Bo having a saddle point at the center of a homogeneous field region designated as the volume 9 in FIG. 1. The field strength may be approximated by the Taylor Series expansion $$B(x,y) = B_o + \tfrac{1}{2} \frac{\partial^2 B_o}{\partial x^2} (x^2 - y^2) \tag{6}$$

Noting that the resonance condition in pulse NMR is met when the deviation of the static field from its center value, $B_o(x,y) - B_o(00)$ is no greater than half the magnitude of the RF field $B_1$, the area of the resonant region can be derived to be approximately $$A_R = 4 \frac{B_1}{\partial^2 B_o/\partial x^2} \tag{7}$$

after making the simplifying assumption that the area has a square cross-section. This and other approximations are made here to more simply illustrate the principles underlying the invention, it being understood that other more exact derivations are obviously possible. Making substitutions for the above equation (5) for the measured NMR signal, we obtain $$V_S = \frac{4\chi Y}{\mu_o} \frac{B_o^2}{\partial^2 B_o/\partial x^2} \left( \frac{B_1}{I_1} \right)^2 I_1 L. \tag{8}$$

It is clear from the qualitative relationships of equation (8) that the measured NMR signal can be made better or worse by changing the various parameters given. However, increasing the signal level is not sufficient, and it is highly desiable to keep the thermal noise level as low as possible, relative to the signal $V_S$. The root mean square thermal noise is $$V_N = (4k\, T Z_o \alpha f)^{\tfrac{1}{2}} \tag{9}$$

where $Z_0$ is the input impedance of the matching network 20 (nominally 50 ohms), k is Boltzman's constant, and $\alpha f$ is the measurement bandwidth, which is matched to the bandwdth of the population of resonated particles in the formation $YB_1/2\pi$. The following ratio of the peak signal to the root mean square noise is obtained;

$$\frac{V_S}{V_N} = \frac{2\chi}{\mu_o} \left( \frac{\pi Y}{\kappa T} \right)^{\tfrac{1}{2}} \left( \frac{B_o^2}{\partial^2 B_o/\partial x^2} \right) \left( \frac{B_1}{P_1^{\tfrac{1}{2}}} \right)^{3/2} P_1^{\tfrac{1}{2}} L \tag{10}$$

In equation (10) the power fed to the antenna, $P_1$, has been substituted for the current using the relationship $P_1 = I_1^2 Z_0/2$. Further, using the conventional definition of the Curie Law susceptibility in MKS units, $$\chi = \mu_o \frac{N\phi Y^2 I(I+1) h^2}{3\kappa T} \tag{11}$$

we obtain the final expression for the signal-to-noise (S/N) ratio $$\frac{V_S}{V_N} = \left[ \tfrac{2}{3} (\pi)^{\tfrac{1}{2}} N\phi Y^{5/2} I(I+1) h^2 \left( \frac{1}{\kappa T} \right)^{3/2} \right] \left[ \left( \frac{B_o^2}{\partial^2 B_o/\partial x^2} \right) \left( \frac{B_1}{P_1^{\tfrac{1}{2}}} \right)^{3/2} P_1^{\tfrac{1}{2}} L \right] \tag{12}$$

In equation (12), the first bracketed expression above depends on enviromental parameters such as the proton spin density of the fluid N, porosity $\Phi$, and absolute temperature T. Some of the other terms are Planck's constant (over $2\pi$) $\eta$, and the nuclear spin I which has a value of $\frac{1}{2}$ for protons. The second bracketed expression contains design parameters which optimize tool performance. For example, it is readily seen that a high static field $B_0$, being a squared term, can immensely improve the S/N ratio.

Furthermore, it is seen that the expression $(B_1/P_1^{\frac{1}{2}})^{3/2}$ which is related to the "Q" of the antenna, should be made large. However, S/N cannot be indefinitely increased by increasing $B_1/P_1^{\frac{1}{2}}$ because equations (10) and (12) hold only when the bandwidth is limited by $YB_1/2\pi$, e.g. when $Q<B_0/B_1$. In contrast, when $Q>B_0/B_1$, the bandwidth is $\Delta f = YB_0/2\pi Q$, and equation (12) becomes $$\frac{V_S}{V_N} = \left[ \tfrac{2}{3}(\pi)^{\frac{1}{2}} N\phi Y^{5/2} I(I+1) h^2 \left(\frac{1}{\kappa T}\right)^{3/2} \right] \left[ \frac{B_0^{5/2}}{\partial^2 B_0/\partial x^2} \cdot \frac{B_1}{P_1^{\frac{1}{2}}} \cdot \frac{1}{Q^{\frac{1}{2}}} \cdot L \right] \quad (13)$$

For a set antenna geometry and measurement point, it is known that the quantity $B_1/P_1^{\frac{1}{2}}$ is directly proportional to $Q^{\frac{1}{2}}$. It is seen from the above that further decreasing the losses of the antenna beyond the point where $Q \leq B_0/B_1$ would not increase S/N.

Referring to FIGS. 1 and 3, the magnet array 17 consists of three samarium cobalt permanent magnets 24, 25, 26, which are mounted parallel to each other within a metal alloy body 27. Magnets 24, 25, 26 are elongated in the direction lonitudinally of the borehole, and measure 12 inches in the preferred embodiment. The magnetic poles of the magnets are not on the smallest faces of the slab, commonly viewed as the ends of a bar magnet; instead, the poles appear on the two opposing edges of the slab magnet and point to the left and right, respectively, in both FIG. 1 and FIG. 3. Thus, within the formation 12, the magnetic field $B_0$ surrounding the magnets remains fairly constant along the longitudinal direction of the borehole axis.

Magnets 24, 25, 26 should be as strong as practical, and should be capable of withstanding physical shock without disintegration. The samarium cobalt magnets that have been used, for example, are preferably enclosed in a sturdy brass casing to prevent any explosive fragmentations in the event the magnet cracks or breaks. These magnets are commercially avilable, and have a residual induction of typically 10,500 gauss. It would be obvious to those skilled in the art that other magnets may be substituted for the samarium cobalt magnets herein, and the slab magnets can have other dimensions than that shown in the preferred embodiment.

It is preferable to use elongated slab magnets to produce a static field in formation 12 which is constant over a substantial distance L along the z coordinate parallel to the borehole axis. A large L improves S/N and also facilitates continuous logging along the z coordinate. However, the magnets should not be so long as to make the tool 13 structurally unwieldy or to cause excessive standoff between the face 14 and the borehole wall in washed out zones.

Magnets 24, 26 are symmetrically mounted in the two sides of the body 27 with the north poles facing the same directions. Magnet 25 is positioned parallel to and between the other two magnets, but with its north poles facing oppositely from magnets 24, 26. Magnet 25 is also shifted slightly away from face 14, relative to magnets 24, 26. As shown in FIG. 3, the north poles of magnets 24, 26 point in the direction of the face of the tool, while the north pole of magnet 25 is pointed away from the face 14, although the configuration obviously may be reversed and still produce a similar result.

Figure 6:
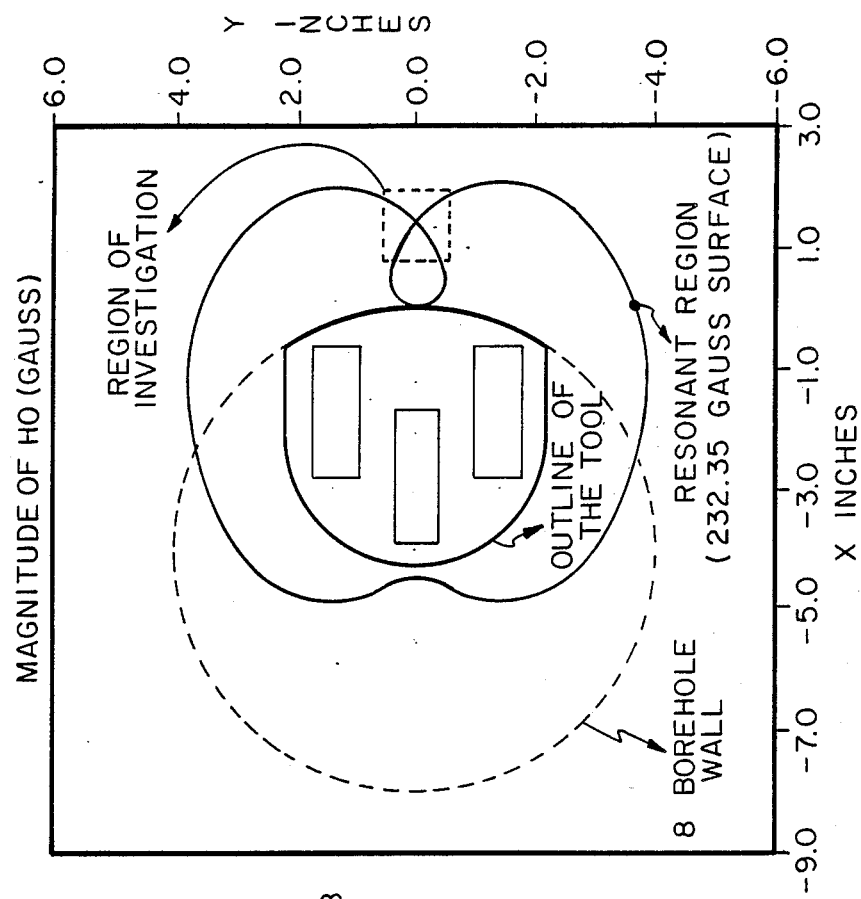
FIG. 6 is a diagram showing the magnetic field $B_0$ equal -magnitude line of 232 gauss, as in FIG. 3-5, also showing the region of investigation of the preferred embodiment shown in FIG. 1.
Figure 4:
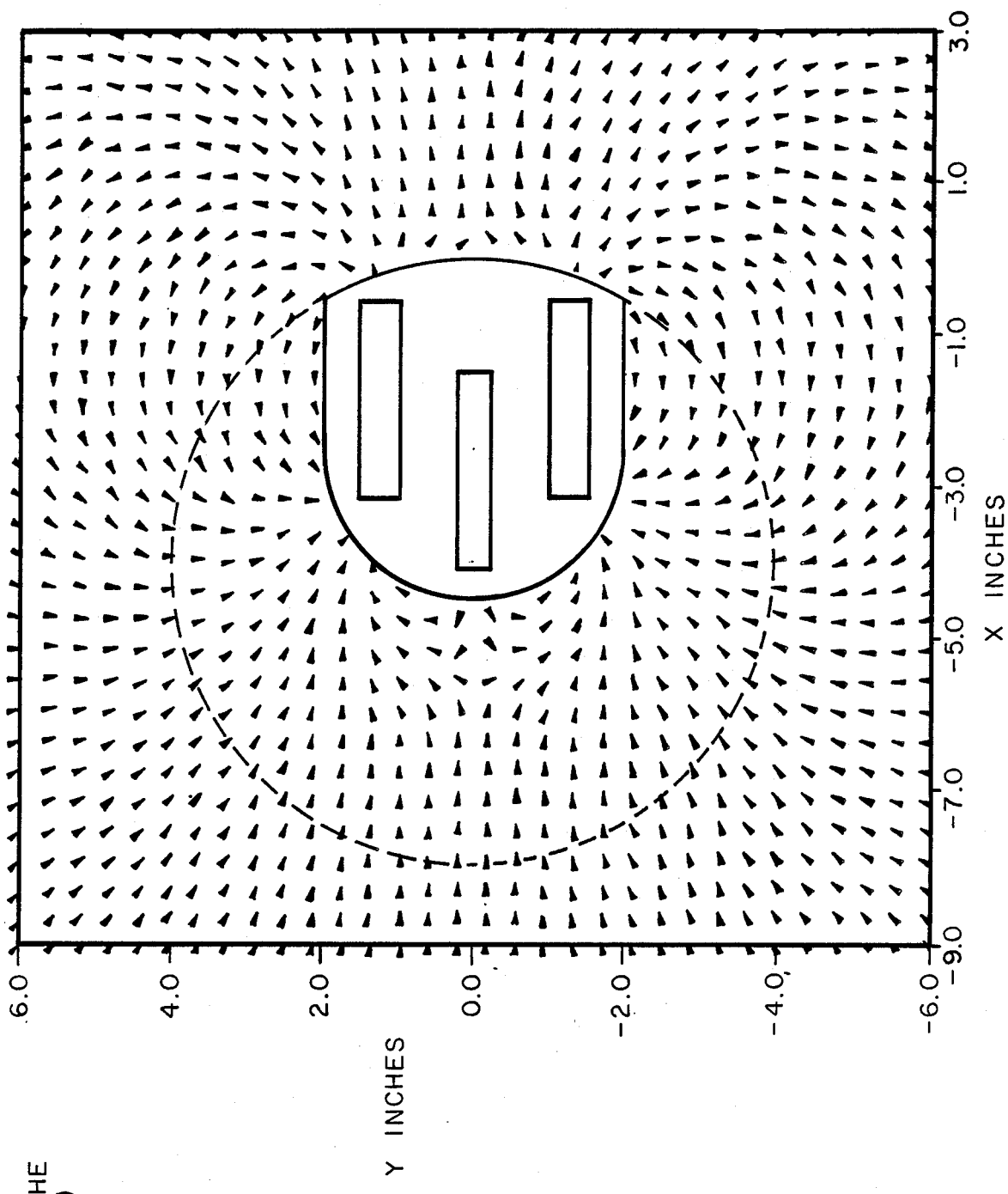
FIG. 4 is a diagram showing the magnetic field lines, represented by arrowheads, surrounding the magnet array of FIG. 3, when placed within a borehole.
Figure 5:
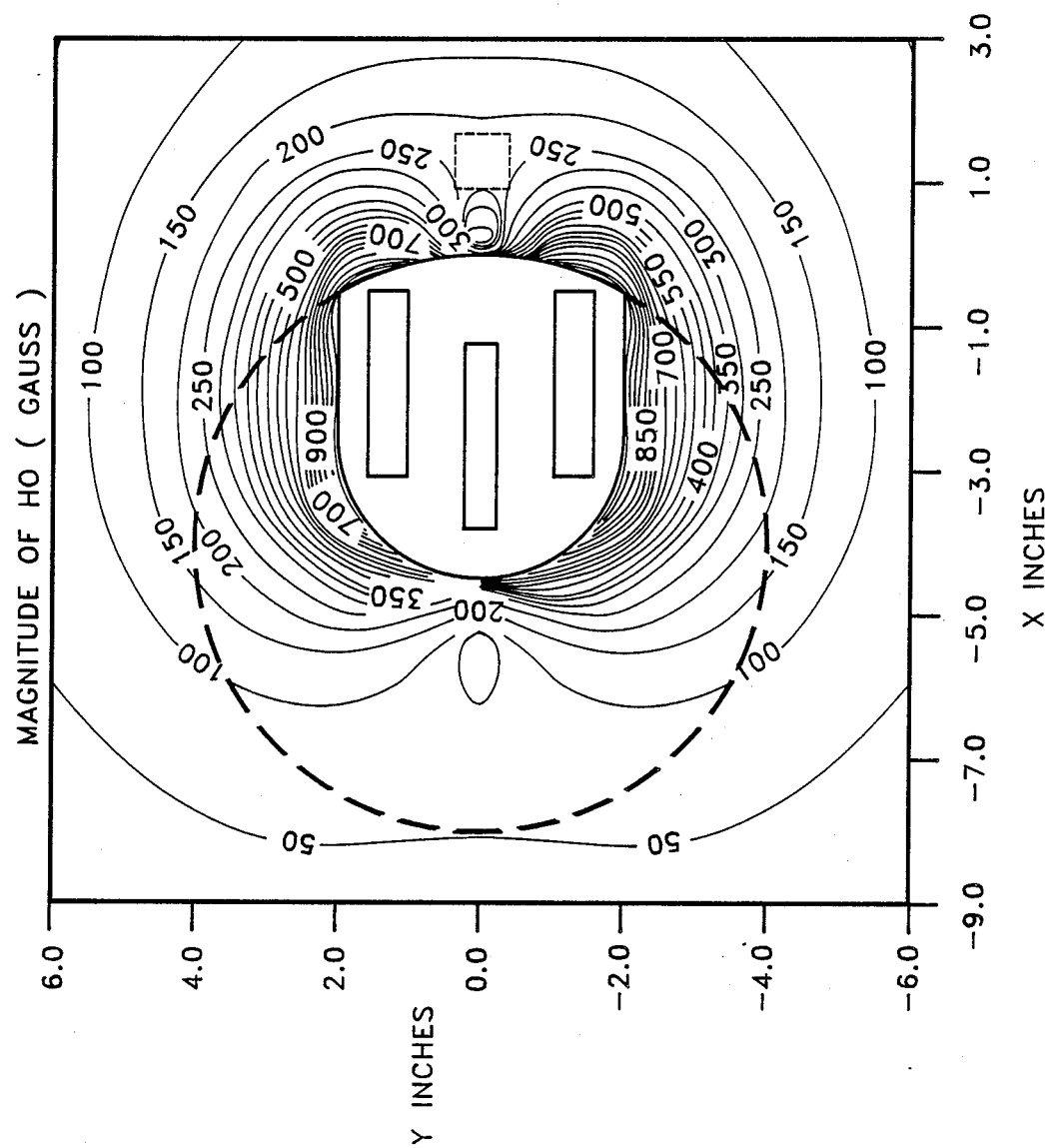
FIG. 5 is a diagram showing, in cross-section, magnetic field $B_0$ equal - magnitude lines of the magnet array shown in FIGS. 3 and 4.

Referring to FIGS. 4–6, it can be seen that, by configuring the two N poles of magnets 24, 26 to point at the face 14 and the formation 12 lying beyond, magnet array 17 would appear at a great distance like a magnetic N pole. However, the reversed pole positioning of magnet 25 substantially alters the magnetic field at close and intermediate distances into formation 12. At intermediate distances, this preferred configuration of magnet array 17 produces an interesting and important field anomaly within a uniquely defined volume directly in front of the tool face 14. As seen in greater detail in FIGS. 5–7 there is a well-defined volume in which the magnetic field is substantially constant, and wherein the spatial gradient of $B_0$ substantially vanishes. This is the primary resonance region for NMR measurements and is the Volume of Investigation shown in FIG. 1.

Figure 8:
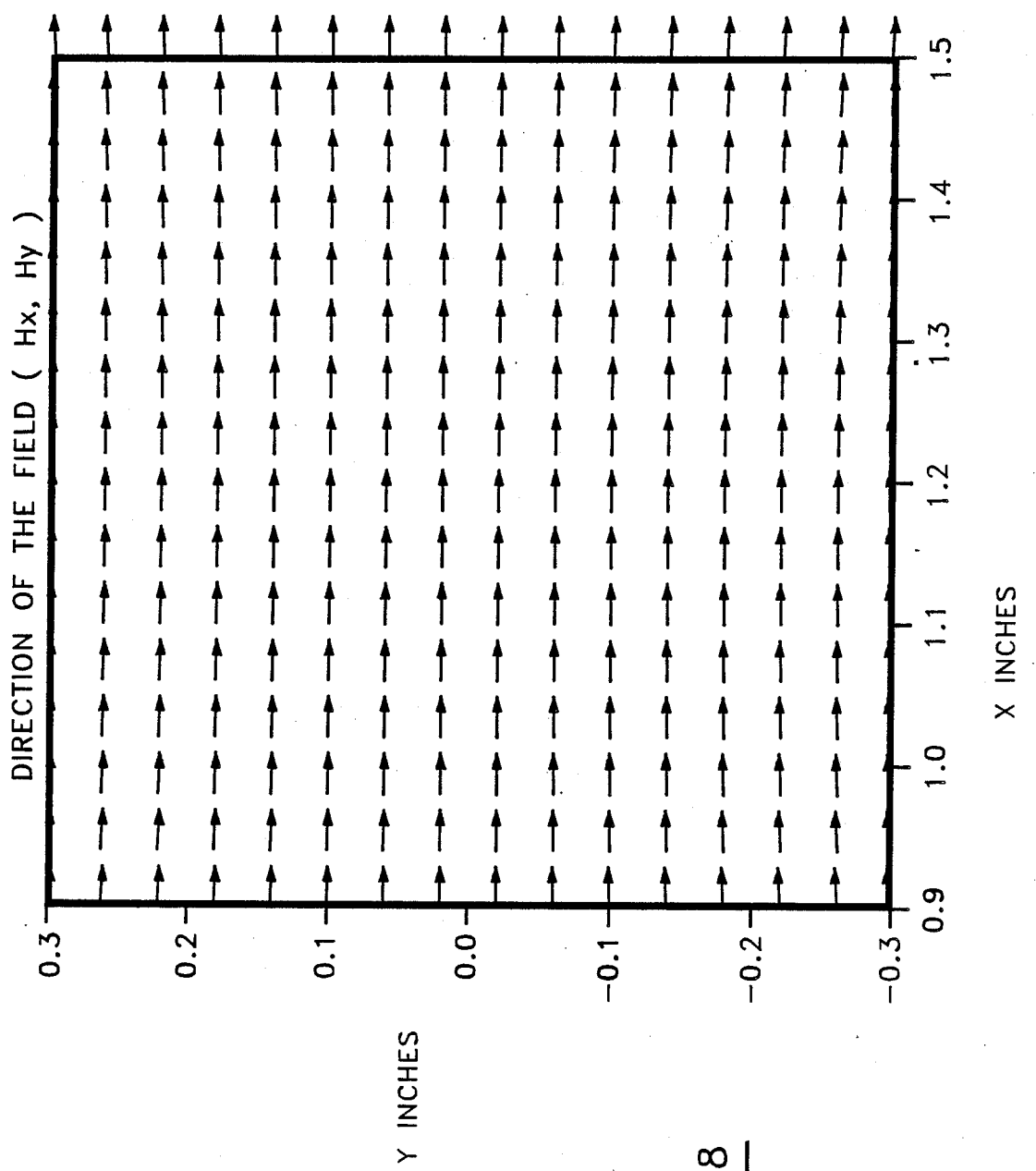
FIG. 8 is a diagram of magnetic field lines showing the vector directions and magnitude of $B_0$ within the region of investigation of FIG. 6.

FIG. 8 shows vector arrows which follow field lines within the cross sectional area approximately one inch from the tool face 14, with the length of each vector arrow proportional to field strength and the direction of each arrow following the field lines. It can be seen that the field $B_0$ projects radially into the formation and that it is quite uniform throughout this area, and has a substantially constant field strength of approximately 232 gauss.

Although the volume of greatest field homogeneity is centered about a point approximately 4/5 inch away from the wall engaging face 14, this volume of substantially homogeneous field can be shifted either a greater or less distance into the formation, depending on the relative positioning, spacing, and field strength of magnet 25 with respect to magnets 24, 26. It is additionally possible, in other embodiments of the invention, to provide for shifting of magnet 25 within the body 27 during operation of the tool so as to obtain a variable depth of investigation, depending on the circumstances. For example, if a formation having high rugosity or an extremely thick mudcake is encountered, the logging engineer may shift the position of magnet 25 a predetermined distance to the right, as seen in FIG. 3 so that the volume of investigation 9 is shifted further into the formation, to avoid obtaining undesirable resonance signals from the mudcake. However, in the preferred embodiment shown in the figures, magnets 24, 25, 26 are rigidly mounted in position since the resultant positioning of the volume 9 already avoids any substantial overlap with the relatively thin mudcake layer of typical boreholes.

Referring again to FIGS. 5, 6 and 7 it can be appreciated that the size of the Volume of Investigation 9 can depend on the nature of the measurement that is taken and the strength of a RF pulse that is transmitted by the antenna 18 as explained hereinbelow.

The metal body 27 has, on the front face 14 thereof, a semicylindrically shaped cavity or slot 28 which faces formations engaged by the face 14. The cavity 28 is adapted for receiving the RF antenna 18, as will be further described below. It is already clearly seen, however, that antenna 18 is positioned outside of the metal body 27 of the tool, and is automatically shielded from electromagnetic communication with regions of the borehole which lie behind the body 27, or regions of other formations in directions intercepted by the body 27. Antenna 18 is thus responsive only to magnetic fields originating in front of the wall engaging face 14, e.g. fields originating in the formation 12 or in the mudcake or mud which contacts face 14 in the vicinity of the antenna 18. By utilizing the relative geometric positioning of the antenna and the metal body 27, it is possible to minimize undesirable signal contributions which would otherwise be difficult to eliminate by other means. In the preferred embodiment, body 27 is made of metal alloy sheathing, rigidly attached to interior metal bracing, which envelops most components of the tool other than the antenna 18, including the circuitry, the magnet array 17, and the hydraulics system of the arm 15. It is also possible for the body 27 to be constructed of other combinations of materials such as composite resins, steel, etc., as long as the overall structure is sufficiently strong, and the magnetic field of the magnet array 17 can penetrate and enter the adjoining formation 12.

Antenna 18 is used both as a RF transmitter to produce a polarizing magnetic field in formation 12, and as a receiving antenna to detect coherent magnetic signals emanating from precessing protons immediately after the polarizing field is terminated. Antenna 18 should be constructed of one or more current carring loops which are highly efficient in generating magnetic fields in the formation. It is preferably made of a current loop which produces an oscillating field $B_1$ within the volume of investigation which is perpendicular to $B_0$. Other current loop orientations may be useful in other embodiments of the invention having a static field $B_0$ differing from that of the preferred magnet array 17.

Antenna 18 is attached to body 27 and fitted within the slot 28. Its efficiency can be ideally maximized when the current density within the slot 28 is made uniform. In practice, optimum antenna efficiency is difficult to achieve, because of various electromagnetic parasitic effects like the "skin effect", the mutual inductive effects between distinct current loops, and electrical effects within individual conductors. The preferred antenna 18 pursuant to the invention comprises a single current loop, in the shape of a trough or slot, as shown in FIG. 9.

Figures 9, 10:
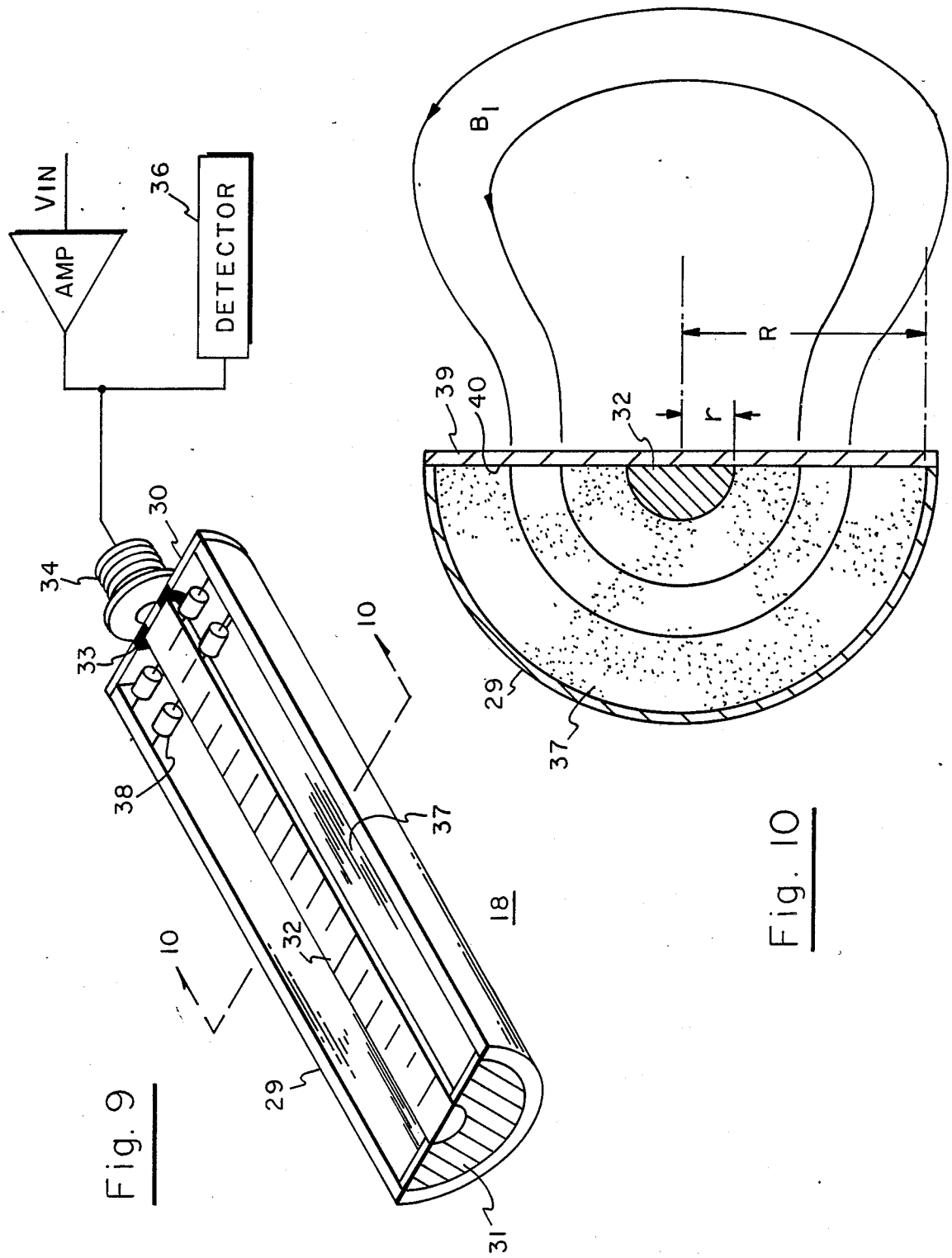
FIG. 9 is a prespective view of an antenna in accordance with the present invention.
FIG. 10 is an enlarged cross-sectional side view of the antenna shown in FIG. 9.

Referring to FIG. 9, the antenna 18 comprises a highly conductive semi-cylindrical cavity or trough 29, end plates 30, 31, and antenna element 32 which extends from one end plate 30 to the other end plate 31, parallel to and centered in the semi-cylindrical trough 29. The trough 29, end plates 30, 31 and antenna element 32 are all preferably made of heavy gauge copper which has extremely low electrical resistance. Antenna element 32 is insulated from end plate 30 by a non-conducting bushing 33 and is connected to an electrical mounting 34 on the other side of end plate 30. Antenna element 32 is attached at its other end to the other end plate 31 so that current passes freely between trough 29 and antenna element 32 via end plate 31. Electrical mounting 34 is shown in FIG. 9 schematically as being connected to circuitry including an amplifier 35 and a detector 36. All connections in antenna 18 are brazed or silver soldered, to ensure a suitably low resistive loss.

RF antenna 18 can be driven by amplifier 35 during specified periods of time, during which it serves as an RF antenna transmitter. Alternatively, at other specified times, antenna 18 is electronically connected to detector 36, during which time it serves as an RF receiving antenna. In certain modes of operation, antenna 18 may be called upon to alternately function as transmitter or receiver in very rapid succession.

The space between trough 29 and antenna element 32 is preferably filled with a nonconductive material 37 having high magnetic permeability. In order to increase the antenna sensitivity Ferrite materials are preferably used. Several tuning capacitors 38 are connected between the base of antenna element 32 and the trough 29, with the capacitances thereof being chosen to produce a LC circuit, with the resonant frequency being the Larmor frequency $\omega_L = YB_0$.

Referring to FIG. 10, the relative dimensions of antenna 18 should be selected to maximize the antenna efficiency. The slot element radius R should be as large as practical, and the spacing R-r should be maximized subject to the condition that r must not be so small as to increase the antenna impedance excessively. It has been found that for a 12 inch trough antenna without ferrite filling, R=0.75 inch and r=0.2 inch produces optimum efficiency. A ferrite filled trough antenna having dimensions R=0.75 inch and r=0.3 inch has been found to be optimum. The length L of the antenna may be the same as the length of the magnet array 17, which is 12 inches in the preferred embodiment, but antenna 18 is preferably about the same length as the resonance region produced by the magnet array 17 in the formation, which is approximately 4 to 8 inches long.

The field $B_1$ produced by antenna 18 is an oscillating magnetic field having a frequency f equal to the resonance frequency of hydrogen nuclei in the sensitive volume of formation where the static field is about 232 gauss. Therefore, $f = (YB_0)/2\pi = 1.0$ MHz. The strength of $B_1$ has direct impact on the bandwidth of precessing nuclei which are resonated by $B_1$ in accordance with the bandwidth formula:

$$\Delta f = (YB_1)/2\pi$$

Since the static field $B_0$ is about 232 gauss in the preferred embodiment, and the antenna generated field strength $B_1$ at 1 inch is 3 gauss, the resultant bandwidth of $B_0$ within the desired volume is also 3 gauss.

Figure 13:
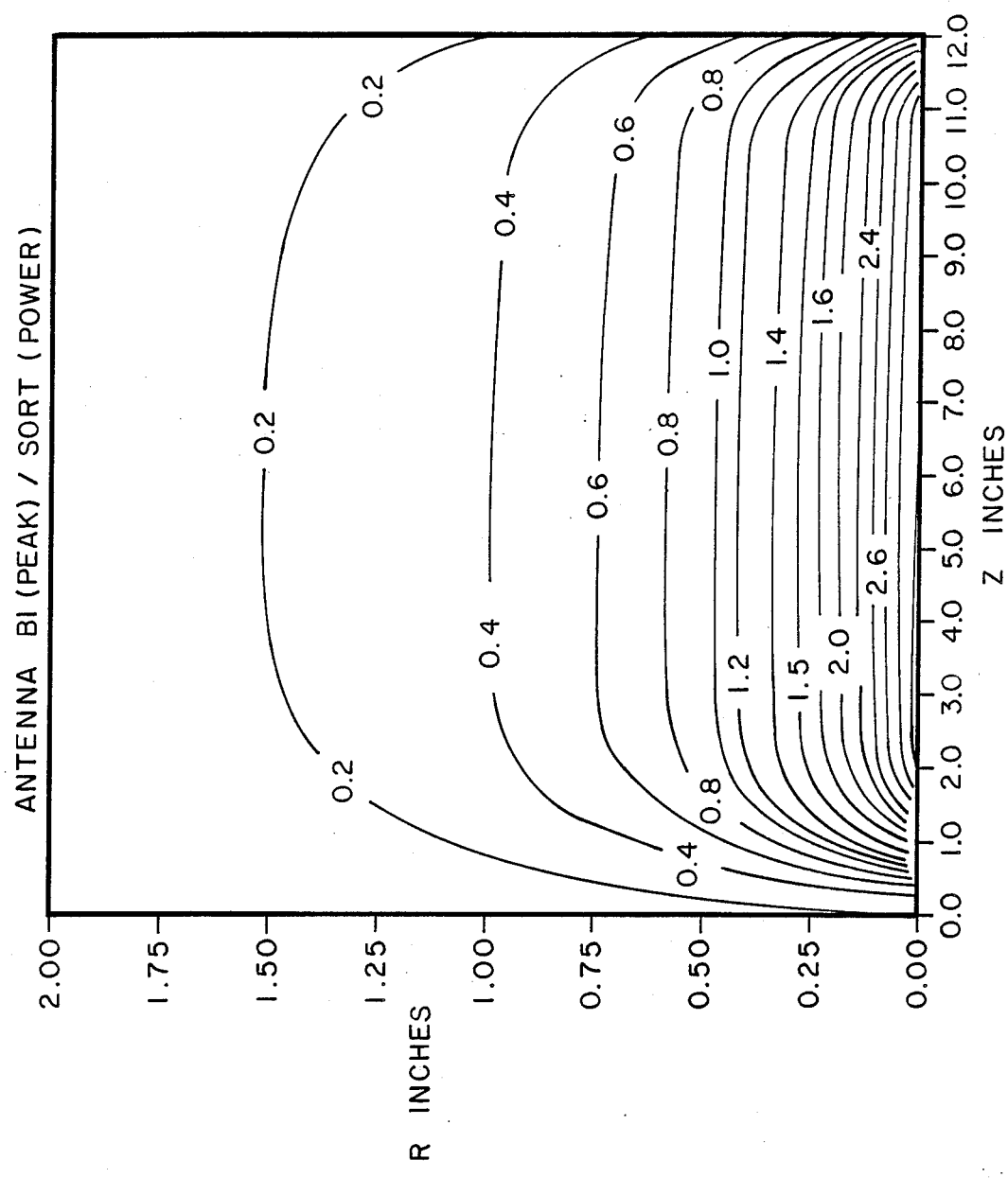
FIG. 13 is a graph of the ratio $B_1$ divided by the square root of the power $P_1$ fed to a preferred embodiment of the antenna of the invention, as in FIG. 1.

The strength of the $B_1$ field in the sensitive volume also affects the S/N ratio (equation 12) in accordance with the term $B_1/P_1^{\frac{1}{2}}$, where $B_1$ is perpendicular to the static $B_0$ field. FIG. 13 shows a plot of the magnitude of $B_1/P^{\frac{1}{2}}$ in front of a 12" trough antenna, where $P_1$ is the power applied to a 50 ohm impedance matching network of the antenna 18 and B1 is the circularly polarized component of the radiated field. It is seen that the field strength is quite constant at 1 inch for a longitudinal distance of about 8 inches.

Referring to FIGS. 3, 10, and 11, antenna 18 is installed in slot 28 and covered with a wear plate 39 made of a non-conductive abrasion resistant material to protect the ferrite material 37 as well as antenna element 32. It is preferred to additionally provide, either under or within the wear plate 39, a thin conducting wire 40 which substantially fills the antenna opening. The wire 40 is preferably arranged in a loop, with a spacing S between wire segments of about $\frac{1}{2}$ inch, although this dimension can be altered if it is desired to spoil magnetic resonance in a local region of greater or lesser thickness. A small D.C. current is passed thru wire 40 at selected intervals during the measurement cycle, generating local inhomogeneous magnetic fields $B_2$ which extend towards the formation 12 for a distance approximately equal to the spacing S between segments of the wire 40. Within this region of local field inhomogeneity, nuclear magnetic precession is disrupted during part of the measurement cycle, and any resonant conditions which were otherwise created by the intersection of $B_0$ and $B_1$ are substantially altered. The wire 40 constitutes one form of a means for creating localized inhomogeneous fields, and other embodiments are clearly possible. For example, multiple wires, coils, or conductive grids may be used.

Figure 7:
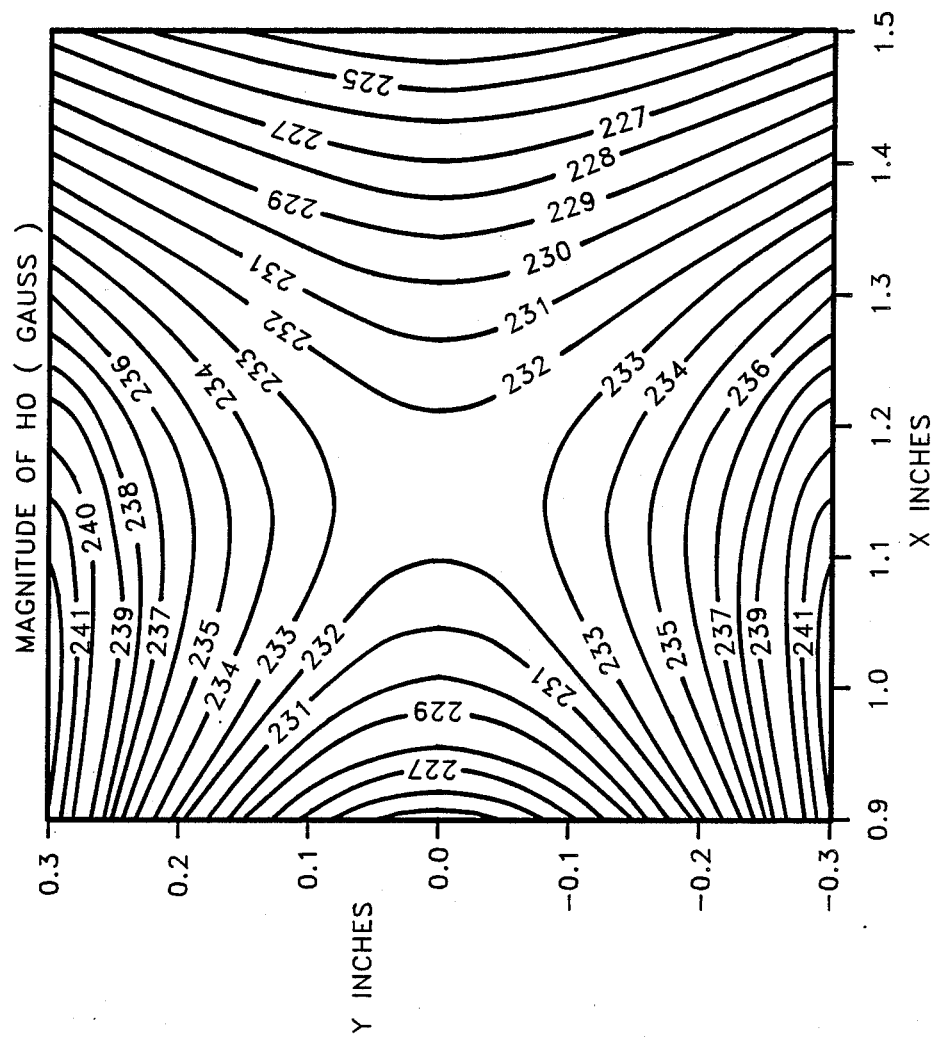
FIG. 7 is a cross-sectional diagram showing magnetic field $B_0$ equal - magnitude lines within the region of investigation shown in FIG. 6.

Spoiling resonance field conditions in the mudcake region is especially advantageous for the preferred embodiment shown in FIGS. 1-8 because typical mudcake contains a high concentration of hydrogen nuclei which may resonate strongly with an applied RF pulse from the antenna 18. The mudcake lying adjacent antenna 18 is subjected to a stronger RF field $B_1$ than even the volume of investigation 9 in formation 12, and therefore may become strongly polarized by $B_1$. Furthermore, there exists high gradient points within $\frac{1}{2}$ inch of the face 14 where the $B_0$ field strength equals the resonant frequency of 232 gauss, as shown in FIGS. 6-7. By imposing the inhomogeneous field $B_2$ within the mudcake region, and spoiling resonance conditions therein, any undesirable NMR contributions from the mudcake are eliminated.

The wire 40 produces a magnetic field $B_2$ having a high spatial gradient $dB_2/dx$, and can alternatively be used to make field gradient type NMR measurements within formation 12. In this case, it would be desirable to arrange the relevant dimensions of wire 40 such that the region of measured NMR resonance overlaps with the gradient field $B_2$.

It is seen that the tool 13 as described measures in a single direction by preferentially directing or "focussing" both the static field $B_0$ and the oscillating field $B_1$, to create the special Volume of Investigation 9. By imposing an additional localized field $B_2$ at regions between the Volume 9 and the tool face 14 which spoils resonance therein, the measurement effectively excludes signals arising from within the mudcake region of the borehole. Furthermore, since the measurement range (distance of sensitivity) of the tool 13 is fairly limited, it is possible to enclose the tool within a reasonably sized calibration cell during testing or calibration of the tool, to exclude magnetic effects of the environment. Consequently, the effective use of the tool 13 for logging oil wells is facilitated.

Electronics

The electronics requirements for the tool 13 may be mounted in the body 27 or in a separate cartridge or sonde. The preferred circuitry, shown schematically in FIG. 12, operates in three modes: transmitting, damping, and receiving.

In the transmitting mode, the circuit 41 must generate a large power of about 1 kilowatt at a frequency on the order of 1 MHz. for a short precisely timed period, shut off this current very quickly, within about 10 microseconds, and then isolate any signals or noise of the power circuits from coupling with other detection circuitry within the tool 13.

Figure 12:
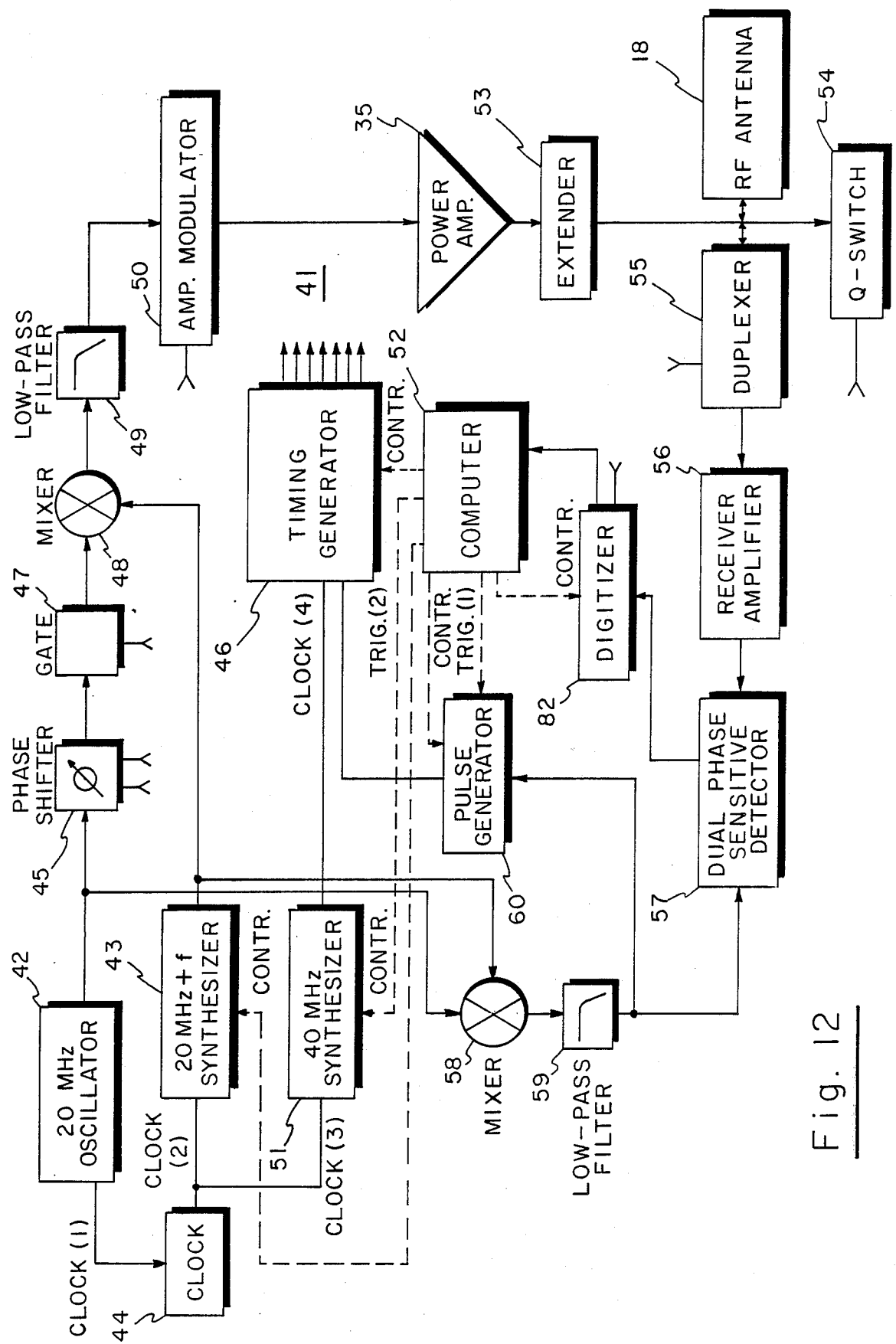
FIG. 12 is a block diagram of circuitry preferably contained in the tool of FIG. 1.

Referring to FIG. 12, the transmitting circuitry comprises a 20 MHz. oscillator 42 and a synthesizer 43 which generates a sinusoidal signal of frequency 20 MHz. +f, where f is the desired frequency of operation of the tool. Both oscillators are linked by a clock 44 and kept in synchronization at all times. The output of oscillator 42 is fed to a phase shifter 45, which is controlled by a timing generator 46. The phase shifter 45 can produce shifts of 0, 90, 180, and 270 degrees, as desired by the operator of the tool, and in accordance with the requirements of various measurement schemes such as the Meiboom - Gill sequence. The phase shifted signal passes through a gate 47, and is then combined with the 20 MHz. +f signal from the synthesizer 43 at a mixer 48. The combined signal is fed through a low pass filter 49 which allows only the signal of frequency f to pass. Although the mixer 48 also has other frequency components at its output, these higher frequency components are filtered out. The desired operating signal of frequency f may be turned on and off at any time by appropriate control of the gate 47 by the timing generator 46. Timing generator 46 is kept in precise synchronization with the clock by a 40 MHz synthesizer. Furthermore the oscillators 42, 43, which have much higher frequencies, may be left running at all times without risk that they would adversely affect the detection circuits which operate at the frequency f.

The f signal, which retains information of the shifted phase, is passed to the amplitude modulator 50 which adjusts the amplitude to change the signal into a desired pulse shape. Both modulator 50 and gate 47, as well as other components in circuit 41, are controlled by timing generator 46 which is in turn controlled by a computer 52. Referring now to FIGS. 14-15, a typical pulse fashioned by the modulator 50 and gate 47 has a first short time interval t(1) where the amplitude has been increased by the modulator 50, and a second short time interval t(2) during which the amplitude is not increased, and a third short time interval t(3) during which the amplitude is increased and the phase of the signal is reversed. The third period of phase reversal may not be necessary where the shaped pulse is already adequately damped by the Q-switch described hereinbelow. The increased amplitude during t(1) helps to decrease the time it takes to ring up the RF antenna 18, while the reversed - phase signal during t(3) helps to kill the ringing in antenna 18 at the end of the pulse. Therefore, the resultant pulse of magnetic field $B_1$ that is radiated into the formation 12 much more closely resembles a square pulse.

The pulse signal from amplitude modulator 50 is amplified by power amplifier 35 which is capable of out putting approximately 1.2 kilowatts without distorting the signal shape. The signal then passes through an extender 53 which prevents low level noise on the order of ten volts or less from leaking out of amplifier 35 when it is not activated, during the receiving mode. The amplified pulses are then fed to the RF antenna 18, radiating a pulse of magnetic field $B_1$ to resonates nuclear spins in the formation. In between transmitting pulses, the RF antenna 18 receives oscillating magnetic signals of nuclear spin precession.

As previously mentioned, the receiving system of RF probe and matching circuit is designed to have a high Q to maximize the S/N ratio. In such a high Q system, the antenna tends to ring for an undesirably long time, and causes undesirable magnetic spin tipping in the formation. If the antenna is permitted to ring uncontrollably, the transmitted magnetic field pulse bandwith may be substantially reduced. In order to minimize the antenna ringing problem, a Q switch 54 is connected to the line between extender 53 and antenna 18 as a preferred means for damping antenna ringing very quickly at the end of a transmitted pulse. The Q switch 54 closes a circuit at the appropriate time, which changes the impedance of the RF probe system (including RF antenna 18) so that the system is critically damped, and the ringing energy quickly dissipated.

During the receiving mode of operation, Q switch 54 is switched off, and signals from precessing nuclei are received by RF antenna 18 and passed through a duplexer 55 to a receiver amplifier 56. Duplexer 55 protects the receiver amplifier 56 from the high power pulses which pass from extender 53 to the RF antenna 18 during the transmitting and damping modes. During the receiving mode, duplexer 55 is effectively just a 50 ohm cable connecting the antenna 18 to receiver amplifier 56. The detected and amplified signal is then passed to a dual phase sensitive detector 57 which also receives a reference signal that controls the frequency of sensitivity of the detector 57.

The reference signal, also having frequency f, is generated by combining the 20 MHz and 20 MHz + f outputs of the oscillator 42 and synthesizer 43 in a second mixer 58, and extracting the lower frequency component f via a low pass filter 59. The output of low pass filter 59, a sinusoidal wave form of frequency f, is used as a reference signal for both the detector 57 and a pulse generator 60. The pulse generator 60 generates an appropriate pulse shape in response to control and triggering signals from the computer 52, and triggers the timing generator 46.

The detector 57, in response to the reference signal and the formation NMR signal from receiver amplifier 56, obtains a measured NMR resonance signal of frequency f from the desired volume of investigation, and passes it to the digitizer 82. The digitized signal is then forwarded to the computer 52 for processing and/or formatting as desired by the operator.

Q - Switch

Figure 16:
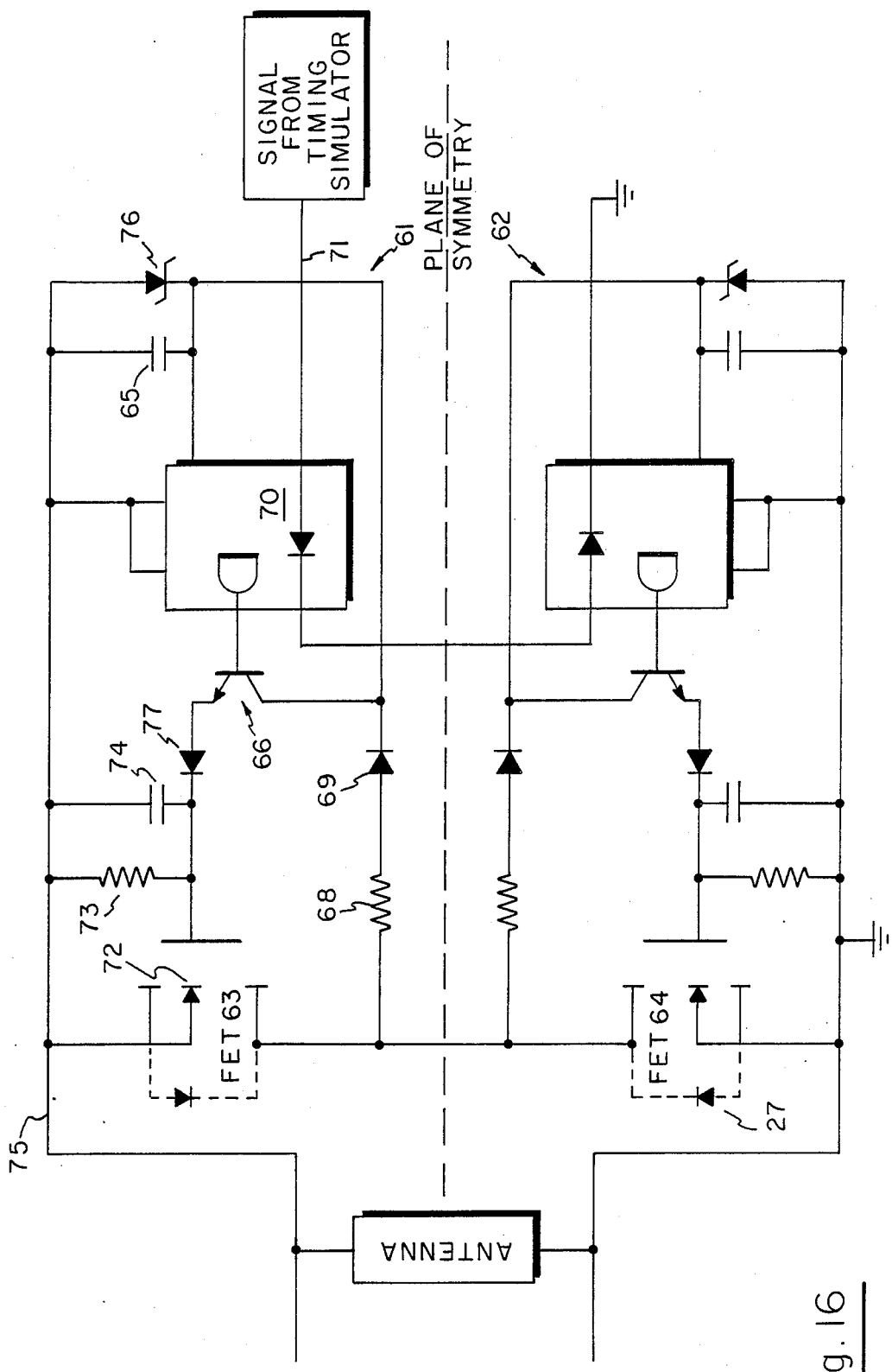
FIG. 16 is a circuit diagram of a Q switch in accordance with the present invention.

Referring to FIG. 16, the Q Switch 54 comprises two symmetric circuits 61 and 62, shown on the top and bottom, respectively of the figure. The purpose of the Q switch 54 is to introduce a resistive element into the antenna network, in parallel with the capacitors 38 (see FIG. 9), so as to critically damp the network, in accordance with the formula $R_C = \frac{1}{2}(L/C)^{\frac{1}{2}}$. For example, where $L = 1.1 \times 10^{-7}$ H., $C = 2.3 \times 10^{-7}$ F. and assuming an operating frequency of 1 MHz, the needed additional resistance to critically damp antenna 18 would be $R_C = 0.36$ ohm.

Q switch 54 utilizes two field effect transistors (FET's) 63, 64 connected back to back, to provide approximately the resistance of 0.36 ohms, when they are closed. Two FET's are needed since each one is effective in developing a resistance to a high voltage therein of only one polarity due to an effective internal diode 67, and the ringing of the antenna 18 is a bipolar oscillating voltage. If the resistive value needed for critically damping an antenna 18 is greater than the resistance of the FET's 63, 64, additional resistive elements may be inserted in series.

When the FET's 63, 64 are switched open, the circuit is an open circuit and has no effect on the antenna network. Thus, Q switch 54 is open during the transmitting mode and during the receiving mode of the circuitry (FIG. 12), and closed during the damping mode which is shown in FIGS. 14-15 as the time period t(3).

The remaining circuitry in FIG. 16 comprise means for gating the FET's 63, 64 on and off with minimum noise being introduced into the antenna network. Since the circuits 61, 62 are essentially identical, only one of them will be described below.

In the transmitting mode, during the RF pulse, a 20 nF capacitor 65 and the collector of an intermediate stage transistor 66 are charged through the line comprising diode 67, resistor 68 (51 ohms) and diode 69, where diode 67 is part of the FET 64 of the lower symmetric circuit 62. The base of transistor 66 is connected to an optical coupler 70 which is controlled by a signal on line 71 from the timing generator 46. The optical coupler 70 is preferably used with the NMR logging tool because it ensures isolation between the switching signals and the high voltage on the antenna.

The emitter of intermediate stage transistor 66 is connected via diode 77 to the gate 72 of the FET 63. The gate 72 is also connected to a 1 k resistor 73 and a 8.2 nF capacitor 74, which are in turn connected to the source line 75, to constitute a R-C combination high pass filter between gate 72 and source line 75. This R-C filter ensures that the source-to-gate voltage never reaches excessive levels during the transmission of an RF pulse and also provides a self-turnoff time constant. A zener diode 76 connected in parallel with the 20 nF capacitor 65 to prevent excessively large voltages from damaging the optical coupler 70.

During the damping mode, a signal from the timing generator 46 is passed via line 71, to activate the optical coupler 70 and charge the base of the intermediate stage transistor 66. The transistor 66 is turned on, causing a voltage to be applied to gate 72, making the FET 63 conductive, and providing damping of the antenna network.

During operation of the tool 13, the operator enters into the computer 52 information respecting the type of measurement sequence to be taken. Computer 52 then sets the sequence of electronic steps needed for the equipment to implement the measurement sequence. The computer 52 controls the timing generator 46 which in turn sends control signals to the various components of circuit 41 to control the polarizing pulse height, length, frequency, relative phases of sequential pulses, receiving mode period and frequency, and the timing of all of the above.

Because the high Q antenna 18 can be rapidly damped after transmitting a 1 kilowatt RF pulse, the tool 13 is capable of resonating a targeted formation 12 with many successive pulses in a short time. The deadtime between a transmitted pulse and the commencing of the receiving mode, about 25 microseconds, is about 1000 times shorter than the deadtime of the previous commercially available logging tool. Using peak power of 100 W, the pulses can have a duration of about 40 $\mu$sec. and it is possible to have as many as 1000 pulses within a measurement cycle lasting 1 second.

In addition to the NMR measurements heretofore known to be performed by the existing commercial logging tool discussed in the previously cited references, a Carr-Purcell type measurement may also be made to measure the transverse relaxation time $T_2$. This sequence is also commonly known as a 180°-90° sequence, where the angles refer to the degree of tipping undertaken by the precessing protons during the measurement process. Other measurement sequences which can be undertaken with the present apparatus include the Meiboom-Gill sequence, as described in the cited Ferrar and Becker textbook, or a 90°-τ-90° sequence of the type described in G. G. McDonald and J. S. Leigh, Jr., "A New Method for Measuring Longitudinal Relaxation," Journal of Magnetic Resonance, Vol. 9, pp. 358-362 (1973), which measures the longitudinal relaxation time $T_1$. It is contemplated that additional types of borehole NMR measurements may be devised in accordance with the invention to advantageously investigate the magnetic properties of earth formations.

Prepolarization

When the tool 13 is used to make continuous logs, without stopping the tool for each measurement, an alternative embodiment may be preferred, to further improve the S/N beyond what has already been discussed. Referring to FIG. 1, a prepolarizing magnet 19 is installed within the tool 13 above the position of the main magnet array 17, to magnetically polarize the formation 11 before the magnet array 17 has reached proximity to it for measurement. The field of the prepolarizing magnet 19 should be similar to that of the magnet array 17 in orientation, but preferably much stronger, so as to polarize a much larger population of nucleii. As the tool is moved up the borehole, magnet array 17 comes into proximity of formation 11, and radiates it with RF pulses. However, because of the prepolarization, a larger number of nuclei are aligned with the field $B_0$ of the magnet array 17 within the volume of substantially homogeneous field, and a correspondingly larger signal is produced.

Figure 17:
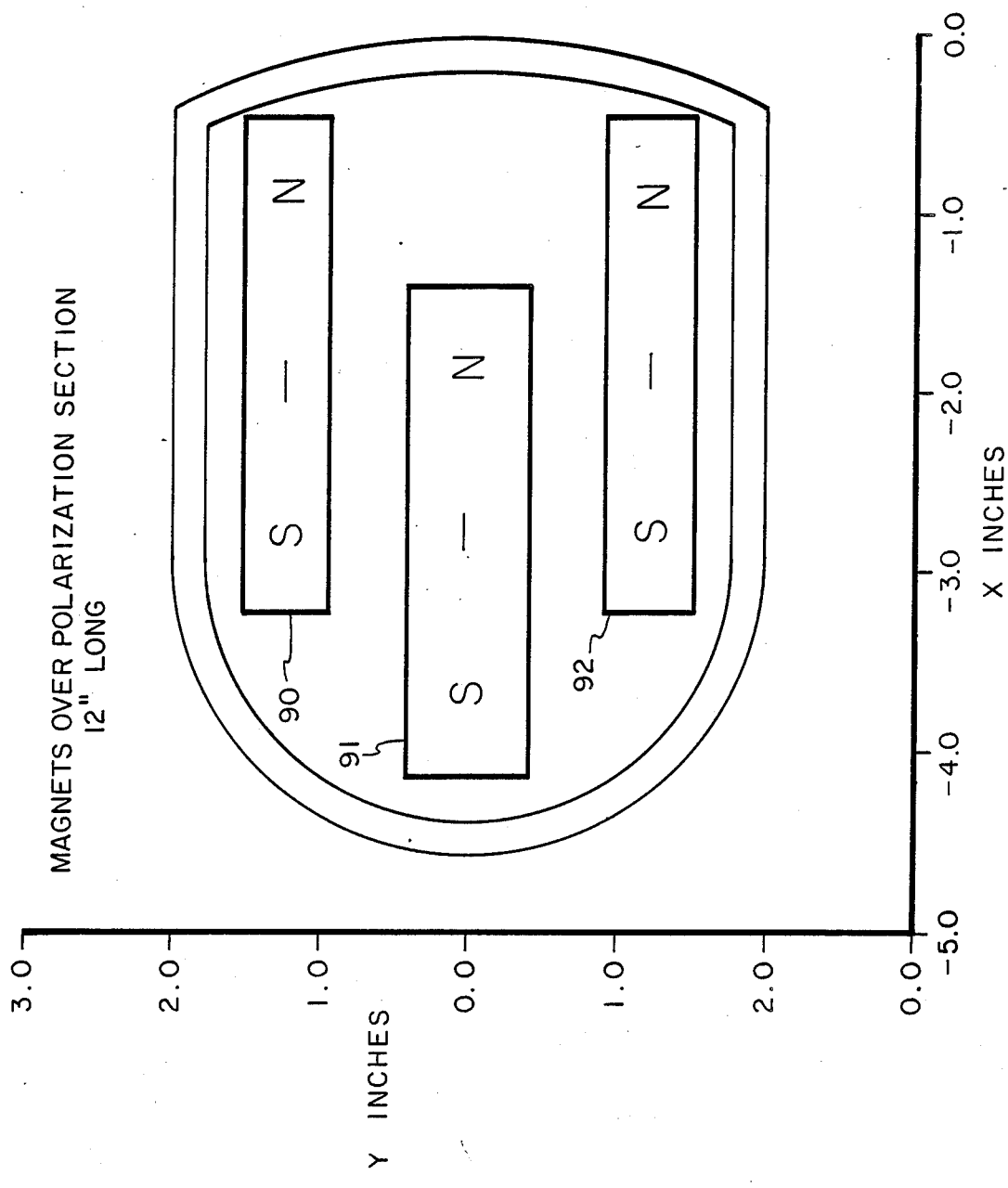
FIG. 17 is an enlarged cross-sectional plan view of a prepolarizing magnet which includes three slab magnets, in accordance with an alternative embodiment of the invention.
Figure 18:
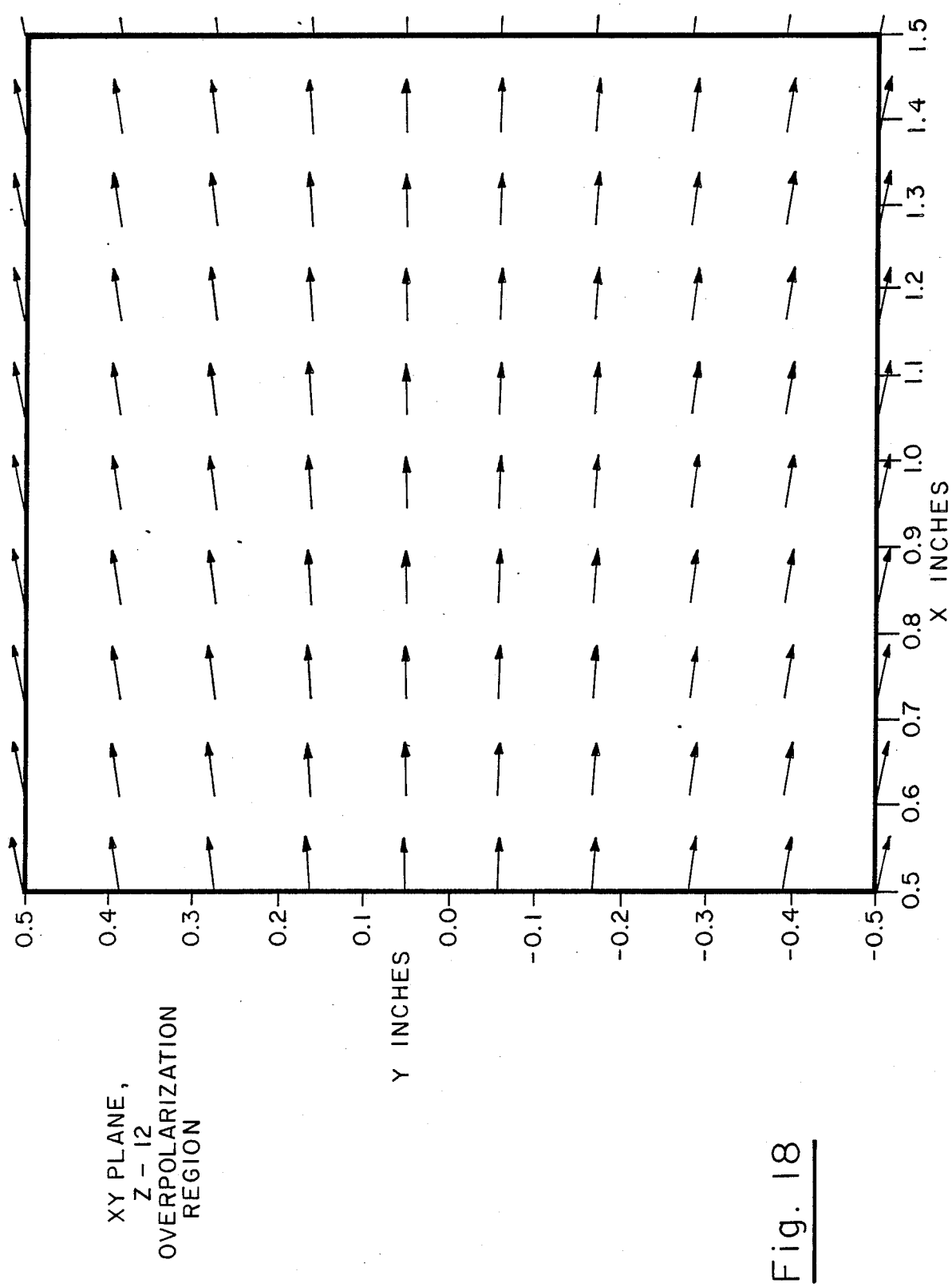
FIG. 18 is a diagram showing the magnetic field lines, represented by short arrows, within a region of investigation in front of the prepolarizing magnet of FIG. 17.
Figure 19:
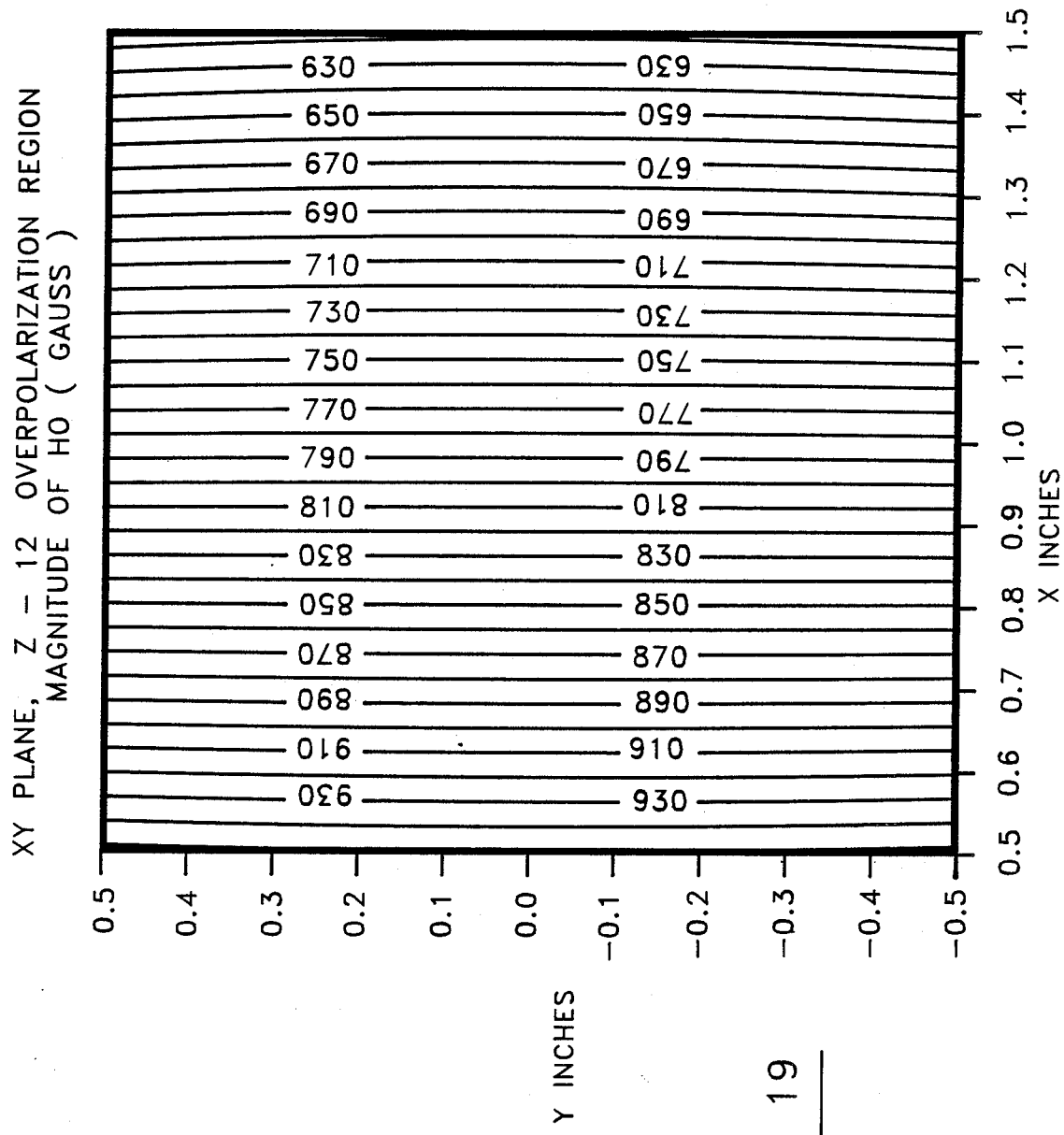
FIG. 19 is a diagram showing magnetic equal-magnitude lines within the region of investigation of FIG. 17.

The prepolarization magnet is preferably an array of magnets in a configuration such as that shown in FIG. 17, comprising magnets 90, 91 92, aligned with similar poles facing in the same direction to maximize the field strength that is produced in the formation. Obviously, other combinations of magnets can produce a similar field, and a single magnet may be used instead of an array as shown. Referring to FIGS. 18-19, the magnetic field $B_p$ of the prepolarizing magnet 19 can be substantially less homogeneous than the field of the magnet array 17, without adversely affecting the bandwith or S/N of the NMR measurement which depends only on the existing static field $B_0$ at the time of the measurement.

The preferred embodiments may obviously be modified in various ways without departing from the spirit of the invention, as would be clear to persons skilled in the art. For example, the prepolarization magnet need not be constructed of the configuration of magnets as shown in FIG. 17, but may be a single magnet or some other arrangement. Slab magnets have been used because the slim profile tends to minimize demagnetization effects, and they are relatively easy to assemble. Since they are large and have very high energy density, the ease of handling and assembly of the magnets are significant considerations, and the simple configuration discussed herein has been found to be advantageous from many standpoints. Nevertheless, other types of magnets may be used, in accordance with the invention.

If stationary measurements are desired, there is the possibility that differential sticking and other dynamic borehole effects would cause the tool 13 to become stuck. Thus, if such stationary measurements are to be made, it is preferable to provide means for prying tool face 14 away from the borehole wall after the completion of a measurement cycle at depth. For example, two push-off pistons 93, 94, shown in FIG. 1 in dotted lines, may be hydraulically actuated to force the tool 13 away from the borehole wall after the arm 15 has been retracted.

Interpretation Methods

The heretofor described apparatus may be used to make measurements of nuclear magnetic resonance in formations surrounding a borehole, to determine formation characteristics such as porosity, pore size, and fluid flow permeability. Various methods of interpretation of NMR logging data, previously known in the art, may be used in conjunction with the disclosed apparatus.

Prior art interpretation of measured NMR decay data concentrated on first deriving a rock formation characteristic such as $T_1$, and then linking it to other formation characteristic of interest such as permeability k. The observed decay time constant of the prior logging tool, $T_2^*$, could not be directly linked to k because $T_2^*$ depended on various magnetic interactions of the environment, the borehole, and the tool which masked the true decay time constant of the hydrogen nuclei of formation pore fluids.

Figure 20:
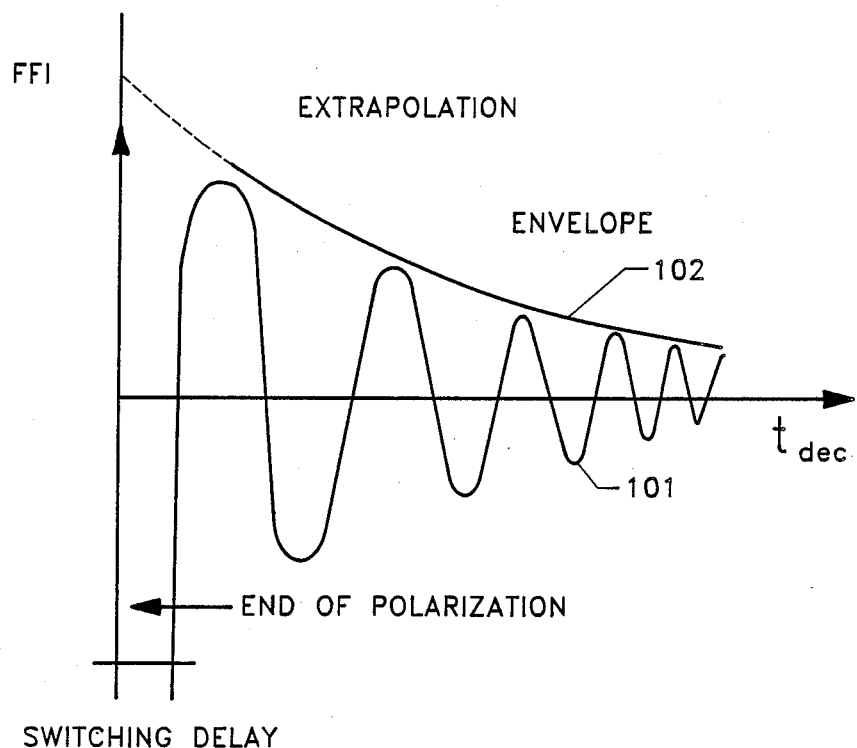
FIG. 20 is a diagram showing a simplified schematic FID signal and its decay envelope, in accordance with prior art interpretation methods.
Figure 21:
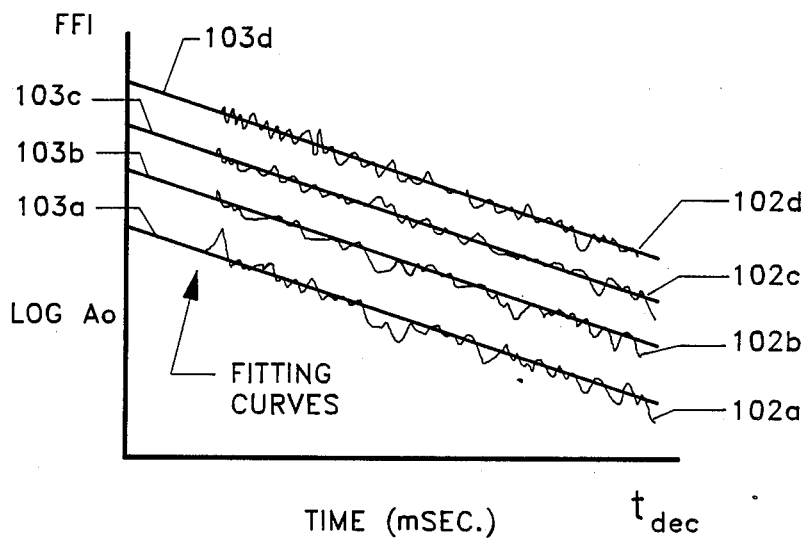
FIG. 21 is a diagram showing four curves representing the decay envelopes of four sets of FID signals (not shown), plotted in semilogarithmic scale in accordance with prior art interpretation methods.

Referring to FIG. 20, the FID waveform or signal 101 represents a signal measured by the prior art tool operating in either the "Continuous Mode" or the "Stationary Mode", and the decay envelope 102 is obtained from the peak values of the FID signal. No signals are received during the "dead time" of approximately 20-30 msec. following the end of each polarizing pulse at time $t_0$. Four such decay envelopes 102a, b, c, and d are shown in FIG. 21, where the FID signals 101 are measured after nonsaturating polarizing pulses having durations $t_{pol}(a)$, $t_{pol}(b)$, $t_{pol}(c)$, and $t_{pol}(d)$, respectively. Note that the envelopes 102 of FIG. 21 show many zigzag points indicative of noise in the signal, whereas FIG. 20 shows a FID envelope 102 which appears smooth because it is a simplified schematic drawing not showing the effects of noise.

Figure 22:
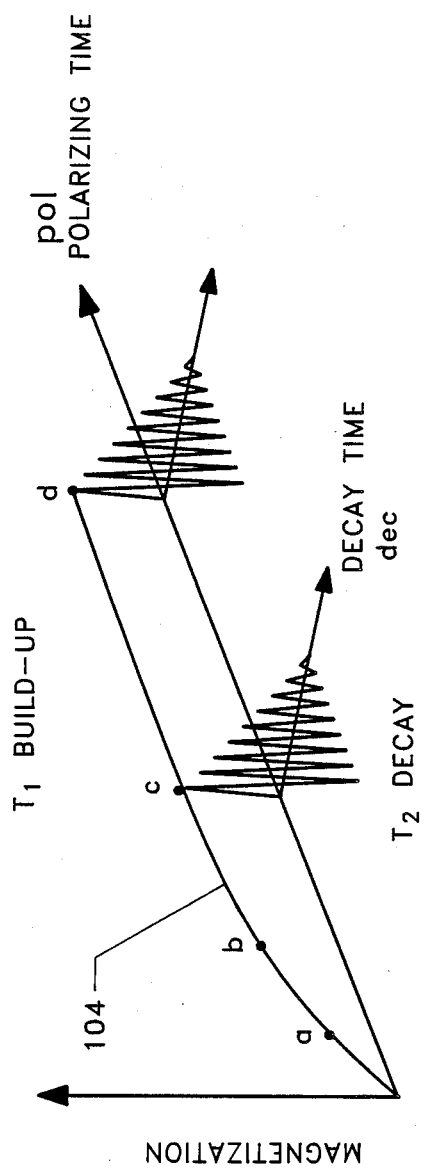
FIG. 22 is a diagram showing a three dimensional representation of multiple sets of FID signals extrapolated to their initial values and constructing a $T_1$ Build-Up curve in the $M(t_{pol})$ plane, in accordance with prior art interpretation methods.

In one prior art method of determining the longitudinal relaxation time $T_1$, each envelope 102 is fitted to an exponential decay fitting curve 103 (shown in FIG. 21) of the form $$A(t_{dec}) = A_0 e^{-t_{dec}/T_2^*} \quad (A)$$

where $t_{dec}$ is the decay time, and $A_0$ is the maximum amplitude of the Free Induction Decay signal at time $t_0$ when the polarizing pulse was initially shut off, and $A(t_{dec})$ is the measured amplitude. The fitting program extracts values of $A_0$ and $T_2^*$ which produce the best fit, and the resulting value of $A_0$ represents the extrapolated ordinate axis intercept at time $t_{dec}(0)$, shown in FIGS. 20-21 as the points FFI. In the prior art method, a second step is required where the extrapolated values are then plotted on a graph of Amplitude $A(t_{pol})$ versus polarization time $t_{pol}$, shown in FIG. 22, which obtains a $T_1$ Build-Up curve 104. Finally this $T_1$ Build-Up curve 104 is fitted to another exponential decay representation typically having the form $\Sigma A_0(1-e^{-t/T_{1i}})$ to extract values for $T_1$.

Figure 23:
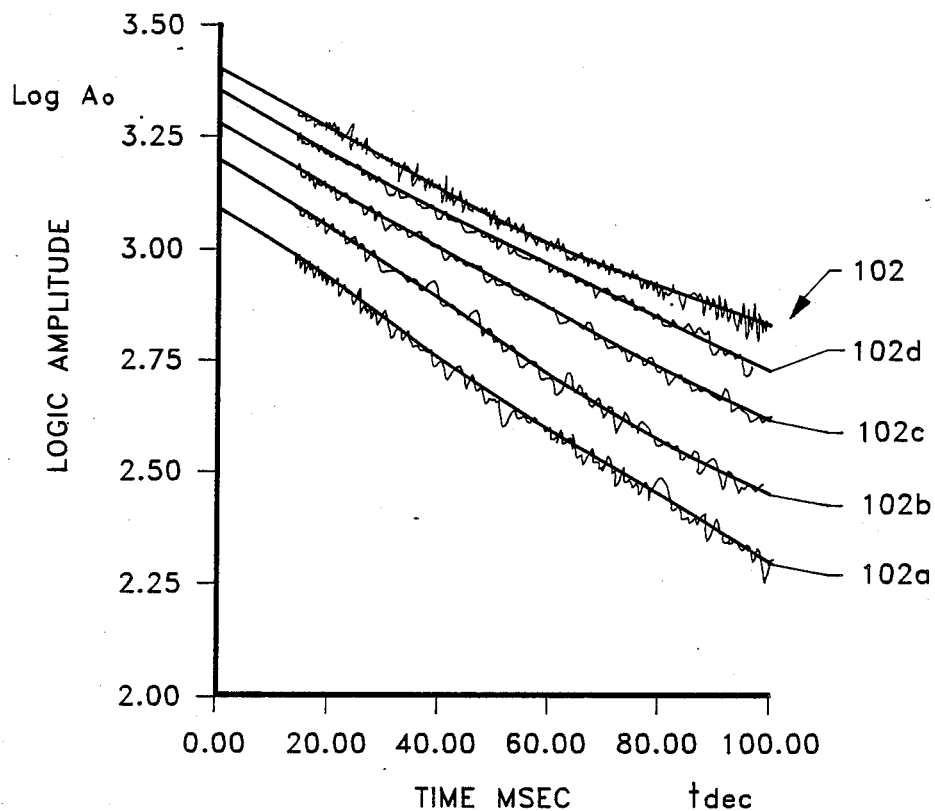
FIG. 23 is a diagram showing eight sets of FID positive peak signals and their corresponding global fitting curves in accordance with a preferred interpretation method of the present invention.

In contrast to the previously known interpretation technique described above, a preferred method of the present invention simultaneously fits the measured data to a model which integrally describes the NMR decay behavior and the changes of that behavior resulting from changes in the degree of initial polarization prior to the decay. This preferred method provides for the simultaneous fitting of the measured amplitudes A by minimizing a fitting quantity of the form $$\Sigma\Sigma[A(t_{pol}, t_{dec}) - A_{REPR}(t_{pol}, t_{dec})]^2 \quad (B)$$

where the representation permits the amplitude $A_{REPR}$ to depend on both $t_{dec}$ and $t_{pol}$ simultaneously. Referring to FIG. 23, a plurality of FID envelopes 102a, 102b, 102c, 102d, etc. are shown, each of which is measured as in the previous FIGS. 20-21, but these envelopes are not individually or separately fitted to a mathematical representation, and no attempt is made to obtain an intermediate extrapolated value of A(t₀) for each envelope, as was done in the prior art. Thus, fitting is accomplished in a single step, in contrast to the two steps of the previous technique.

Those parameters of amplitude and $T_1$ in the model which give the best fit to the measured data are extracted and directly used for interpreting the data. The best fit is preferably obtained by a least squares type fitting computer program which performs iterative numerical minimization of the squared fitting quantity (also known as the fitting error). For example, a program called "ZXSSQ" which is well known in the art and is commercially available from the IMSL Company, Houston, Texas, may be used. Because the fitting is accomplished simultaneously with respect to both the NMR decay response and the differential responses due to different initial polarizations ($t_{pol}$), in a single step (in a "global" approach), the extracted parameters $A_i$ and $T_{1i}$ are considerably more robust and less affected by signal noise.

Three exemplary representations are described below, which illustrate the preferred global method of the invention. A general form for these representations, which include amplitude and $T_1$ parameters is:

$$A(t_{pol}, t_{dec}) = \Sigma A_i [i - e^{-t_{pol}/T_{1i}}] e^{-t_{dec}/T_{2i}^*} \quad (C)$$

where $t_{pol}$ is the time during which the formation is subjected to a polarizing magnetic field, before a decay signal is measured. $T_{1i}$ is the longitudinal relaxation time of the i-th species or component of measured particles, and $T_{2i}^*$ is the observed relaxation time of the i-th species or component.

In particular, as a first preferred representation of the global approach of the invention, the measured amplitudes of the FID signal 101 are represented by a sum of two exponential terms:

$$A_o(t_{pol}, t_{dec}) = \sum_{i=1,2} A_{oi} [1 - e^{-t_{pol}/T_{1i}}] e^{-t_{dec}T_{2i}^*} \quad (D)$$

The two exponent representation is based on the assumption that the formation may be regarded as containing two species of protons, each species having a distinct decay component with maximum amplitude $A_0$, longitudinal relaxation time $T_1$ and transverse relaxation time $T_2^*$. The additional subscript i=1, 2 designates the two components—one component characterized by short time constants for $T_1$, $T_2^*$, and the other component by long time constants. This condition results in the observed decay time constant $T_2^*$ to be dependent on the polarizing period $t_{pol}$. Thus, the global method recognizes that $T_2^*$ is a function of $t_{pol}$ and the envelopes 102a, 102b, 102c, 102d, etc. are not parallel and may not have the same curvature in FIG. 23. Furthermore, by simultaneously fitting all of the decay envelopes using the $A_i$ and $T_{1i}$ parameters, without intermediary fitting steps (as in the prior art), the present method increases the amount of information contributing to the fit, thus obtaining parametric values that are considerably more robust and less affected by noise in the data.

In a second preferred representation in accordance with the invention, the six parameters of equation (D) are reduced to five by assuming that the value for each $T_{2i}^*$ is related to the corresponding $T_{1i}$ through a common parameter $T_{inh}$ defined by:

$$\frac{1}{T_{2i}^*} = \frac{1}{T_{1i}} + \frac{1}{T_{inh}} \quad (E)$$

The parameter $T_{inh}$ is a time constant representing an additional decay mechanism resulting from magnetic field inhomogeneities which are common to both species of the representation. Thus, the representation of equation (D) is reduced to:

$$A(t_{pol}, t_{dec}) = e^{-t_{dec}/T_{inh}} [A_S (1 - e^{-t_{pol}/T_{1S}}) e^{-t_{dec}/T_{1S}} + A_L (1 - e^{-t_{pol}/T_{1L}}) e^{-t_{dec}/T_{1L}}] \quad (F)$$

Using this five parameter representation, it is possible to obtain relatively robust values of $A_S$, $A_L$ and $T_{1S}$, $T_{1L}$ which can then provide information of the permeability or some other desired characteristic of the measured formation. In many cases, the five parameter model fits data as well as the first model which has six parameters.

Other representations may be used with the global fitting method, which further reduce the number of parameters and thereby improve the dependability of the estimated results when processing data having relatively low Signal/Noise. In particular, a third representation having only four fitting parameters is given by $$A(n, t_{dec}) = e^{-t_{dec}/T_{inh}} A_0 [e^{-(t_{dec}/T_1)^\alpha} - e^{-((t_{dec}+t_{pol})/T_1)^\alpha}] \quad (G)$$

where the four parameters—A, $T_1$, a, and $T_{inh}$—are used to obtain a full description of the NMR decay. This model assumes that longitudinal relaxation behavior is described by a "stretched exponential" form:

$$A(t_{pol}) = A_0 e^{-(t_{pol}/T_1)^\alpha} \quad (H)$$

This form arises when nuclear magnetization is composed of a distribution of an infinite number of distinct exponentials from as many distinct species of magnetic particles, where the assumption is made that $T_{2i}^*$ and $T_{1i}$ are inter-related as in the second model. The "stretched exponential" representation has the advantage that it can extract relaxation time parameters with comparable accuracy as the other models in some cases, but with even greater resiliency to problems arising from low Signal/Noise in the data. We have found the stretched exponential to describe laboratory measured rock $T_1$ data somewhat better than the two exponential representation in spite of having less parametric terms.

The three preferred embodiments of the global fitting method described above have been applied to data obtained from formation samples, and the results are presented in Table 1 of the attached paper entitled "Compact and Consistent Representation of Rock NMR Data for Permeability Estimation," by W. E. Kenyon, P. I. Day, C. Straley and J. F. Willemsen, which was presented at the 61st *Annual Technical Conference and Exhibition of the Society of Petroleum Engineers*, on October 5–8, 1986 in New Orleans, LA; this paper is incorporated in its entirety herein by reference.

After extracting values of the relaxation times, $T_1$, $T_2$, and/or $T_2^*$, it is usually desirable to use these values for determining other characteristics of the measured formation, such as fluid permeability k. Several methods for determining k are known in the art, and will not be discussed in detail herein, since they are well documented in the technical literature. For example, Seevers has proposed using an estimator of permeability of the form $k \propto \Phi T^2$, where $T = (T_b \cdot T_1)/(T_b - T_1)$ and $T_b$ is longitudinal relaxation time of the bulk fluid in the absence of pore surface effects, Seevers, D. O., "A Nuclear Magnetic Method for Determining the Permeability of Sandstones", *Society of Professional Well Log Analysts Transactions* (1966) Paper L, whereas Timur has proposed the alternative estimator $k \propto \Phi \Sigma A_i T^2$, Timur, A, "Pulsed Nuclear Magnetic Resonance Studies of Porosity, Moveable Fluid, and Permeability of Sandstones", *Journal of Petroleum Technology* (1969), 775–786.

However, in accordance with the methods of the present invention, the values of longitudinal relaxation time $T_1$ are preferably used in an estimator of permeability of the form $k \propto \Phi^m T_1^n$ where the exponent m is approximately 4 and n is approximately 2. For example, Table 2 of the appended Kenyon et al. paper shows that the optimum estimator for the measured samples of formation rocks is $m = s_2 = 4.61$ and $n = s_1 = 2.09$ used in conjunction with the stretched exponential representation. Table-2 also shows that the global methods of the invention, when used in conjunction with the preferred estimator defined herein provides considerably better determination of permeability of the measured rocks compared with the prior art methods.

Another aspect of the present invention, hereinafter called the "integration method", is directed to the determination of formation characteristics in situations where it is desirable to minimize the measurement time (e.g. to permit continuous logging runs). In these situations it is preferable to minimize the number of parameters to be extracted from the available data, for reasons to be explained below. In a preferred form, referring to FIG. 24, the values of amplitude (representing magnetization) are integrated with respect to the time axis $t_{pol}$ to obtain a single integrated quantity having the units of $\Phi$ T.

In the case of a $T_1$ Build-Up curve 104 or some comparable representation of NMR decay response, the curve 104 is integrated to obtain the area above the $T_1$ Build-Up curve, which is equal to the area under the corresponding decay curve. This integrated quantity, having units equivalent to $\Phi T_1$, is then used in conjunction with an appropriate estimator to obtain a measure of permeability. Preferably, the integrated quantity is squared to obtain $(\Phi T_1)^2$, and then multiplied by $(\Phi_t)^{m-2}$ where $\Phi_t$ is a porosity measured by using some other known borehole logging tool such as those commonly known as neutron-porosity tools. Other estimators may similarly be used, as previously described. The integrated quantity is a more robust representation of the available low S/N data because it is less responsive to the exact shape of the curve 104, and therefore less responsive to errors which are introduced by the mathematical fitting of NMR data having significant levels of noise.

Figure 24A:
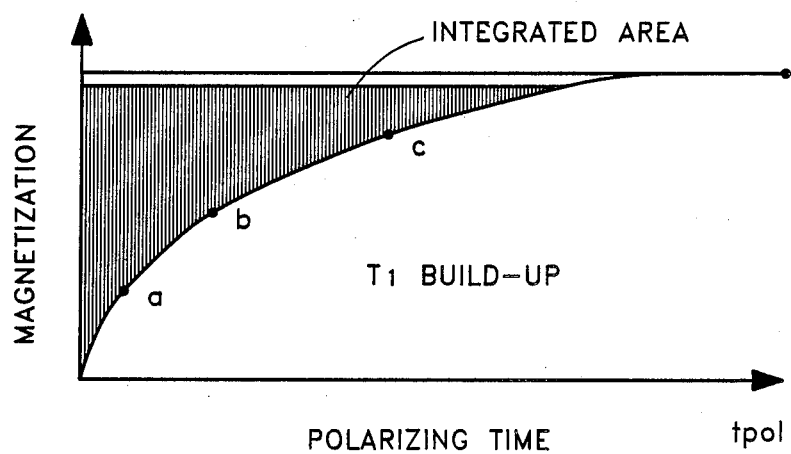
FIG. 24A and 24B are diagrams of a $T_1$ Build-Up curve, as in FIG. 22, but additionally showing integration of the curve in accordance with another preferred interpretation method of the invention.
Figure 24B:
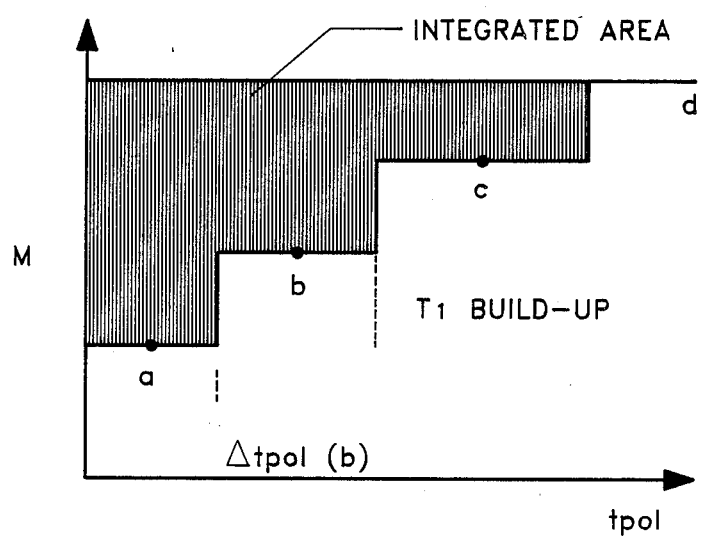

The integration of the curve 104 may be accomplished by various methods which would be obvious to those skilled in the art. FIG. 24 B shows an example of integration by a simple summation of separate products of the form $\Sigma A_i \cdot \Delta t_{pol}$. Similarly, the measured NMR decay signals can be integrated with respect to decay time to obtain an integrated quantity containing information indicative of formation characteristics, which is relatively immune to signal noise or other fine features of NMR decay.

Although the figures are shown with the amplitude axis scaled as the logarithm of A, and the time axis scaled linearly, the present interpretation methods are not intended to be limited to any particular presentations of data. In alternative embodiments, the methods may be implemented with altered scales for amplitude and time. For example, the time axis may be scaled as the square root or some other transformation thereof.

The global fitting method which has been described with reference to the FID signals obtained with the prior logging tool can be equally applicable to data obtained with the pulsed NMR tool of the present invention. For example, a pulsed spin-echo type measurement, such as the Carr-Purcell sequence shown in FIG. 25, yields a series of pulses, the successive peaks of which define a $T_2$ relaxation curve. If several such sequences of measurements are made, with each sequence commencing with a different degree of initial polarization ($t_{pol}$), it is possible, in accordance with the present invention, to determine the longitudinal relaxation time $T_1$. Thus, any one of the preferred representations of the global fitting method can be similarly used to extract values of amplitude and $T_1$ and these extracted values can then be used to determine other characteristics of the measured formation.

Figure 25:
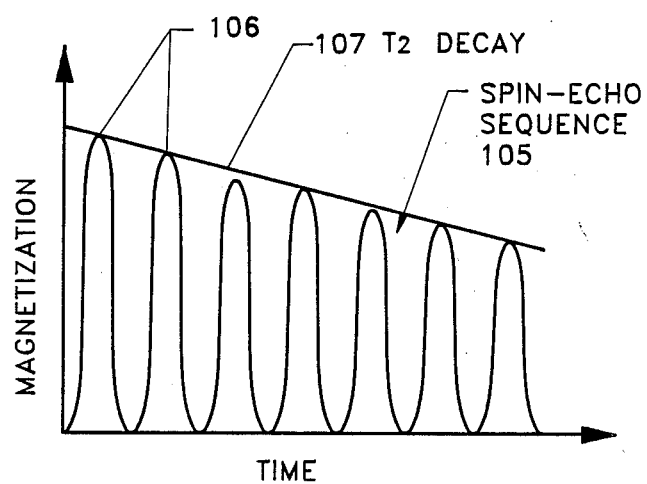
FIG. 25 is a diagram showing a series of spin-echo measurements which can be made by the preferred apparatus of the invention shown in FIGS. 1-15, and further showing the integration of the curve in accordance with another preferred interpretation method of the invention.

Similarly, the integration methods of the invention may also be used to better interpret measured signals from the new tool when it is desirable to minimize the measurement time. In these situations where the data set has relatively low S/N, it is preferred to integrate under the echo signals, as shown in FIG. 25, and to determine the permeability in response to the obtained area in the manner already discussed above.

The NMR logging apparatus of the present invention produces a static homogeneous magnetic field within a Volume of Investigation, as previously described, and superposes oscillating pulses of RF fields which resonantly tip the spins of protons within the Volume of Investigation. By successively imposing pulses $B_1$ in accordance with the Carr-Purcell sequence, the tool 13 directly measures NMR decay having $T_2$ time constant, and is thus capable of directly measuring this formation pore fluid characteristic without the intermediary measurement of $T_2^*$ decay signals, as was required of the previous logging tool.

Figure 27:
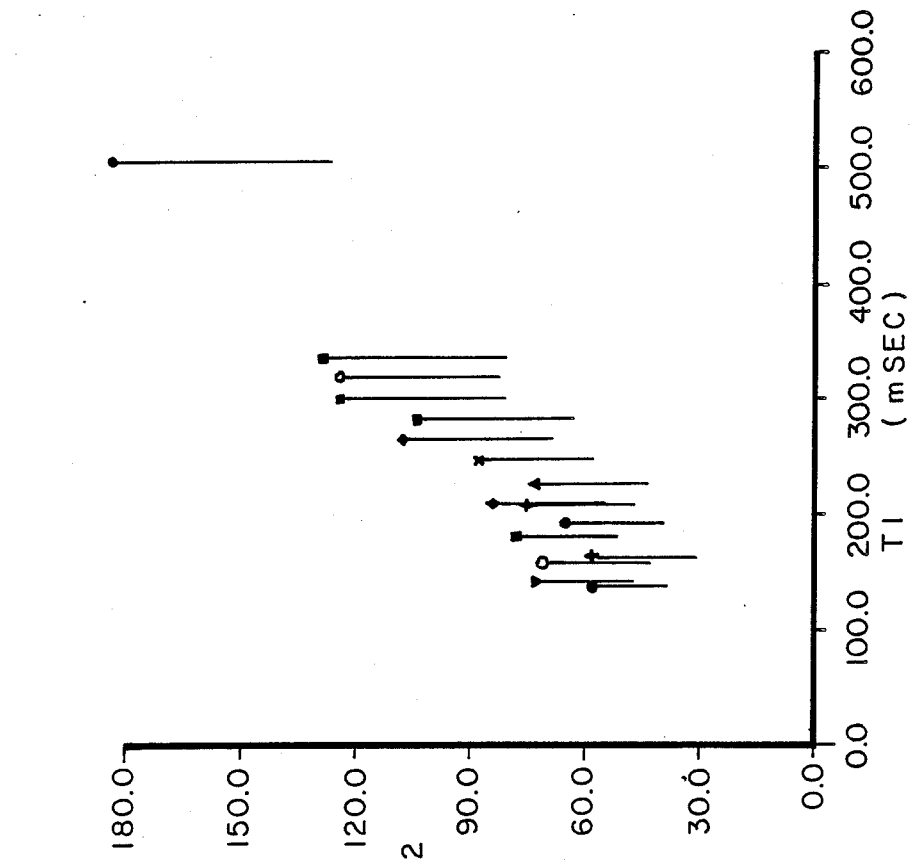
FIG. 27 is a chart showing laboratory measurements of $T_1$ and $T_2$ of actual rock samples from different formations traversed by a second exemplary oil well, similar to FIG. 26.
Figure 26:
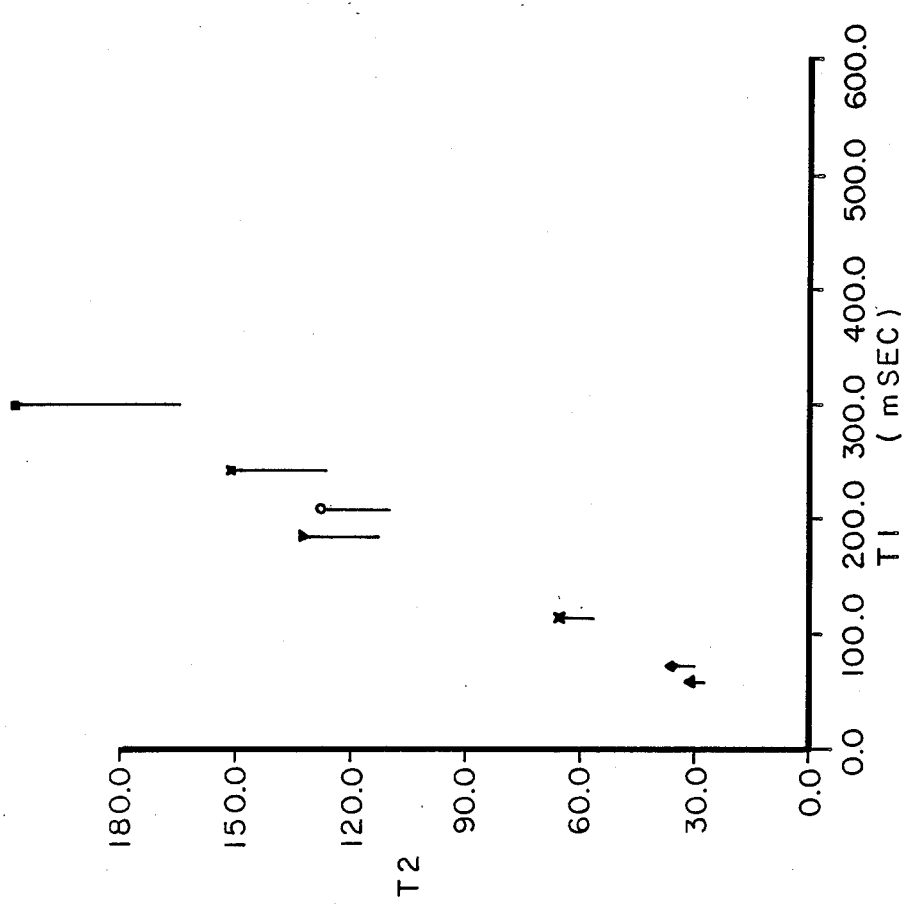
FIG. 26 is a chart showing laboratory measurements of $T_1$ and $T_2$ of actual rock samples from different formations traversed by an exemplary oil well, with each data point also showing a bar representative of relative errors in the measurement of $T_2$ due to internal magnetic inhomogeneities within the rock samples.

Because there exist methods for using information of $T_1$ to determine other formation characteristics, it is a preferred method of the invention to measure NMR decay signals having a characteristic $T_2$ time constant, convert such measurements to hypothetical values of $T_1$ using a transformation $F_T$, and then to use the values of $T_1$ to determine permeability k or like characteristics of the measured formation. Applicants have found, through laboratory measurements of rock samples from different wells, that $T_1 = C \times (T_2)$ where C is a constant for each well, as exemplarily shown in FIGS. 26–27.

Thus, it is preferable to obtain a stationary measurement of both $T_1$ and $T_2$ at a predetermined depth in a well by using, e.g. the Carr-Purcell sequence, determining the constant of proportionality C and then continuously logging the remainder of the borehole to obtain fast measurements of $T_2$. The values of $T_2$ are transformed into $T_1$ values by multiplying by the constant C. Finally, the $T_1$ values are used in conjunction with one of the preferred methods of the invention or other comparable methods to determine the permeability of formations at each of the corresponding depths of the $T_2$ measurements.

Applicants have found that at low NMR frequencies, the values of $T_1$ and $T_2$ converge; it is thus preferred at sufficiently low measurement frequencies to equate the measured $T_2$ data to a hypothetical set of $T_1$ data, and to determine permeability by applying the measured $T_2$ data directly to $T_1$ estimators. Furthermore, other $T_1$ and $T_2$ associated quantities may be similarly transformed. For example, referring to FIG. 25, the integrated area of the Carr-Purcell sequence 105 is computed and used in place of the integrated area of the $T_1$ Build-Up curve to determine permeability, as previously described.

Although the preferred methods of the invention have, for the most part, been described with particularity with respect to the determination of permeability, it is clear that these methods can be similarly used to determine other useful characteristics of rock formations traversed by a borehole, such as fluid viscosity, water saturation and porosity.

It has been described and illustrated herein novel apparatus and methods for measuring and interpreting magnetic characteristics of formations traversed by a borehole. Those skilled in the art will recognize that numerous variations and modifications may be made without departing from the scope of the present invention. Accordingly, it should be clearly understood that the forms of the invention described hereinabove are exemplary, and are not intended as limitations on the scope of the present invention, which should be defined only by the claims appended hereto.

We claim:

1. A method of determining a characteristic of an earth formation traversed by a borehole comprising the steps of:
   1. measuring nuclear magnetic resonance decay signals representative of transverse ($T_2$) or observed ($T_2^*$) magnetic relaxation of a population of particles in the formation following a plurality of different magnetic polarization periods;
   2. selecting a set of values of said signals;
   3. comparing the set of values directly to a representation of NMR decay which includes amplitude A and longitudinal relaxation time $T_1$ terms and simultaneously depends on both the decay time $t_{dec}$ and polarization periods $t_{pol}$ associated with said values;
   4. generating values of amplitude and $T_1$ parameters which optimize the fit between the compared set of values and said representation;
   5. determining the formation characteristic in response to the generated values of at least one of the terms—amplitude or $T_1$.

2. A method as in claim 1 wherein said third step comprises comparing the selected signal values to a representation of the form $$A(t_{pol}, t_{dec}) = \Sigma A_i [i - e^{-t_{pol}/T_1i}] e^{-t_{dec}/T_2i^*} \quad (C)$$

wherein $A(t_{pol}, t_{dec})$ is the signal amplitude, $t_{pol}$ is the duration of a polarizing magnetic field preceding a given measurement, $t_{dec}$ is the decay time at which a measurement is taken, i is the index of magnetic resonance species, $A_i$ is the signal amplitude of a given species, $T_{1i}$ is the longitudinal relaxation time of a given species, and $T_{2i}$ is the transverse relaxation time constant of a given species.

3. A method as in claim 2 wherein said third step comprises comparing the measured signals to a two component representation of NMR decay in the formation, having the general form:

$$A_o(t_{pol}, t_{dec}) = \Sigma A_{oi} [1 - e^{-t_{pol}/T_1i}] e^{-t_{dec}/T_2i^*} \quad (D)$$

4. A method as in claim 2 wherein said third step comprises comparing the measured signals to a representation of the general form:

$$A(t_{pol}, t_{dec}) = e^{-t_{dec}/T_{inh}} [A_S (1 - e^{-t_{pol}/T_1S}) e^{-t_{dec}/T_1S} + \quad (F)$$
$$A_L (1 - e^{-t_{pol}/T_1L}) e^{-t_{dec}/T_1L}]$$

wherein the subscript S designates a first component of NMR decay, L designates a second component of NMR decay, and $T_{inh}$ is a fitting parameter.

5. A method as in claim 2 wherein said third step comprises comparing the measured signals to a representation of the form:

$$A(n, t_{dec}) = e^{-t_{dec}/T_{inh}} A_o [e^{-(t_{dec}/T_1)\alpha} - \quad (G)$$
$$e^{-((t_{dec}+t_{pol})/T_1)\alpha}]$$

where $T_{inh}$ is a fitting parameter, and $\alpha$ is an exponential parameter 6. A method of determining a characteristic of an earth formation traversed by a borehole comprising the steps of:
   1. measuring NMR decay signals representing magnetic relaxation of a population of particles in the formation following a plurality of different magnetic polarization periods;
   2. generating, in response to the measured signals, a representation of a characteristic relaxation of the population of particles, in the form of magnetization versus time;
   3. integrating said representation of magnetization versus time to obtain an integrated value; and
   4. determining said characteristic of the formation in response to the integrated value.

7. A method as in claim 6 further comprising:
   measuring $T_2^*$ decay signals following a plurality of different polarizing periods;
   determining, from the measured signals, a $T_1$ build-up curve of magnetization versus polarizing period; and
   integrating said build-up curve to obtain said integrated value.

8. A method as in claim 6 wherein said measurement step further comprises measuring the magnetization of said population of particles by using a spin-echo sequence of measurements whereby the successive peaks of the spin-echo signals decay with time constant $T_2$, and further comprising converting said integrated value to an integrated value associated with $T_1$ relaxation, and determining said characteristic of the formation using said integrated value associated with $T_1$ relaxation.

9. A method as in claim 8 wherein the measuring step further comprises measuring said magnetization at low resonance frequencies.

10. A method as in claims 6, 7 or 8, further comprising: generating a value representing the porosity of said formation; determining permeability of said formation in response to said integrated value and the square of the porosity value.

11. A method as in claim 8 wherein said spin-echo sequence comprises a Carr-Purcell sequence.

12. A method of determining a pore fluid characteristic of an earth formation traversed by a borehole comprising:
  1. measuring, with a borehole tool, NMR decay signals representative of transverse relaxation of a population of particles in said formation exhibiting a $T_2$ relaxation time constant;
  2. generating a first representation of said signals;
  3. converting said representation into a second representation associated with the longitudinal relaxation time constant $T_1$ of said population of particles;
  4. determining said formation characteristic in response to said second representation.

13. A method as in claim 12 wherein said second representation is a multiplicative factor of said first representation.

14. A method as in claim 12 further comprising: measuring NMR decay signals with a borehole tool positioned stationarily at a predetermined first depth within the borehole; generating a value representative of the longitudinal relaxation time $T_1$ of a formation at said first depth in response to said NMR decay signals; measuring additional NMR decay signals with said tool in continuous motion at other depths within said borehole; generating additional values representative of the transverse relaxation time $T_2$ of formations at said other respective depths in response to said additional signals; determining a characteristic of said formations at said other respective depths in response to both said additional values and said value representative of $T_1$.

15. A method as in claim 12 wherein said borehole tool measurement is made at low frequencies, and said second representation is identical to said first representation.

16. The method as in claims 1, 6 or 12 wherein the formation characteristic is formation permeability, and wherein this characteristic is proportional to a product of (constant)$\cdot \Phi^m \cdot T^n$ where porosity $\Phi$ is raised to the power m being approximately 4, and T is one of said relaxation parameters raised to a power n.

* * * * *

UNITED STATES PATENT AND TRADEMARK OFFICE
CERTIFICATE OF CORRECTION

PATENT NO. : 4,933,638                    Page 1 of 3

DATED : June 12, 1990

INVENTOR(S) : W.E. Kenyon et al.

It is certified that error appears in the above-indentified patent and that said Letters Patent is hereby corrected as shown below:

Title sheet, item [73], the Assignee's name should be -- Schlumberger Technology Corp.--.
   Col. 3, line 16 "contributes" should be --contribute--.
   Col. 5, line 48 after "magnetization" there should be a period.
   Col. 12, line 33 "desiable" should be --desirable--.
   Col. 12, line 42 "bandwdth" should be --bandwidth--.
   Col. 13, line 46 "avilable" should be --available--.
   Col. 22, line 18 "characteristic" should be --characteristics--.
   In the drawings, Fig. 1, reference numeral 18 should be applied to the half-solid and half-dashed antenna on magnetic array 17.
   In the drawings, Fig. 2, the word "INPENDANCE" should be --IMPEDANCE--.
   In the drawings, Fig. 3, the polarity of the central magnet should appear as follows:

UNITED STATES PATENT AND TRADEMARK OFFICE
CERTIFICATE OF CORRECTION

PATENT NO. : 4,933,638
DATED : June 12, 1990
INVENTOR(S) : W.E. Kenyon et al.

It is certified that error appears in the above-indentified patent and that said Letters Patent is hereby corrected as shown below:

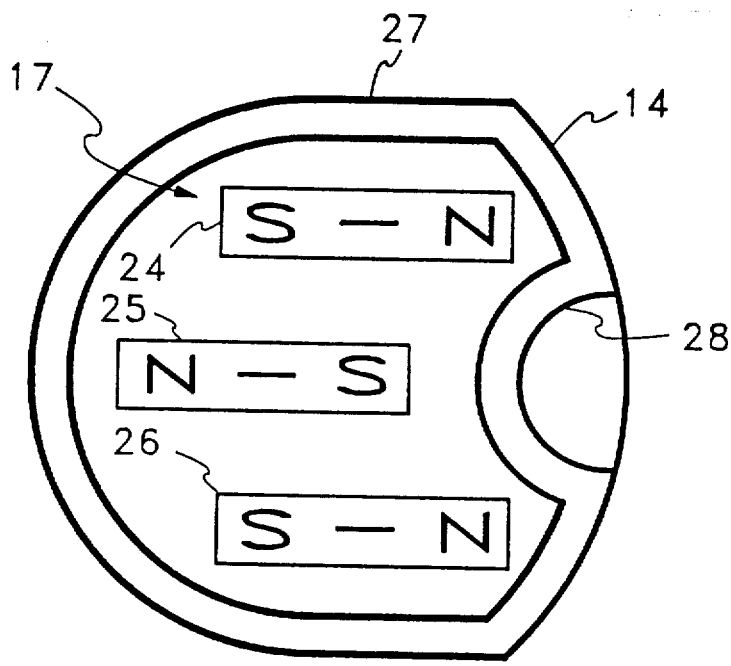

UNITED STATES PATENT AND TRADEMARK OFFICE
CERTIFICATE OF CORRECTION

PATENT NO. : 4,933,638

DATED : June 12, 1990

INVENTOR(S) : W.E. Kenyon et al

It is certified that error appears in the above-indentified patent and that said Letters Patent is hereby corrected as shown below:

In the drawings, Fig. 6, "8 BOREHOLE" should be --8" BOREHOLE--.
    In the drawings, Fig. 13, the curve labelled "1.5" should be labelled --1.6--, and the curve labelled "1.6" should be labelled --1.8--.
    In the drawings, Fig. 17, on the vertical axis the three lowest labels, in descending order, should be -- -1.0 --, -- -2.0 --, and -- -3.0 --.
    In the drawings, Fig. 22, "pol" should be --$t_{pol}$--, "$T_2$" should be --$T_2^*$--, and "dec" should be --$t_{dec}$--.
    In the drawings, Fig. 23, "LOGIC" should be --LOG 10--.

Signed and Sealed this

Thirty-first Day of May, 1994

Attest:

BRUCE LEHMAN

Attesting Officer     Commissioner of Patents and Trademarks